US011596722B2

(12) United States Patent
Guttman et al.

(10) Patent No.: US 11,596,722 B2
(45) Date of Patent: Mar. 7, 2023

(54) FLOW CAPTURE DEVICE AND METHOD FOR REMOVING CELLS FROM BLOOD

(71) Applicant: CAPTEC MEDICAL KFT., Budapest (HU)

(72) Inventors: Andras Guttman, San Diego, CA (US); Gabor Jarvas, Veszprém (HU); Márton Géza Szigeti, Budapest (HU)

(73) Assignees: CAPTEC Medical Kft., Budapest (HU); Pannon Egyetem, Veszprém (HU)

( * ) Notice: Subject to any disclaimer, the term of this patent is extended or adjusted under 35 U.S.C. 154(b) by 858 days.

(21) Appl. No.: 16/321,015

(22) PCT Filed: Jul. 28, 2017

(86) PCT No.: PCT/HU2017/050032
§ 371 (c)(1),
(2) Date: Jan. 26, 2019

(87) PCT Pub. No.: WO2018/020285
PCT Pub. Date: Feb. 1, 2018

(65) Prior Publication Data
US 2021/0316053 A1      Oct. 14, 2021

Related U.S. Application Data

(60) Provisional application No. 62/367,650, filed on Jul. 28, 2016.

(51) Int. Cl.
*A61M 1/16*      (2006.01)
*A61M 1/36*      (2006.01)
(Continued)

(52) U.S. Cl.
CPC ........ *A61M 1/1627* (2014.02); *A61M 1/3679* (2013.01); *B01D 61/243* (2013.01);
(Continued)

(58) Field of Classification Search
CPC .... A61M 2202/0478; A61M 2202/203; A61M 2202/206; A61M 2206/11; A61M 1/1627;
(Continued)

(56) References Cited

U.S. PATENT DOCUMENTS 6,039,946 A      3/2000   Strahilevilz
8,057,418 B2   11/2011   Korbling et al.
(Continued)

FOREIGN PATENT DOCUMENTS

EP      2504083 B1 *   8/2017
GB      2479536 A      10/2011
(Continued)

OTHER PUBLICATIONS

Gaitas et al.: "Chemically Modified Plastic Tube for High vol. Removal and Collection of Circulating Tumor Cells", PloS one, 2015, 10(7), e0133194, pp. 1-11.
(Continued)

*Primary Examiner* — John Kim
(74) *Attorney, Agent, or Firm* — Jason D. Voight

(57) ABSTRACT

Flow capture device and method for removing cells from blood The current invention discloses a blood treating and/or purifying device for removing circulating pathogens, preferably pathogenic cells, more preferably circulating tumor cells from the blood of a patient, a method of producing such a device and method to treat cancer and other diseases caused by virus infection, bacterial infection and parasites infection as well as autoimmune disorders. The described method is an extracorporeal medical therapy, thus can be done also in a hemodialysis system. The current invention also describes a device and an in-situ production method of preparing the device to remove CTC and other pathogens i.e. virus, bacteria or parasites from the bloodstream.

15 Claims, 10 Drawing Sheets

(51) Int. Cl.
*B01D 61/24* (2006.01)
*B01D 69/08* (2006.01)
*B01D 69/14* (2006.01)
*B01D 67/00* (2006.01)

(52) U.S. Cl.
CPC ......... *B01D 67/0088* (2013.01); *B01D 69/08* (2013.01); *B01D 69/081* (2013.01); *B01D 69/144* (2013.01); *A61M 2202/0478* (2013.01); *A61M 2202/203* (2013.01); *A61M 2202/206* (2013.01); *A61M 2206/11* (2013.01); *B01D 2323/30* (2013.01); *B01D 2323/36* (2013.01)

(58) Field of Classification Search
CPC . A61M 1/3679; B01D 61/081; B01D 61/243; B01D 67/0088; B01D 69/08; B01D 69/144; B01D 2323/30; B01D 2323/36
See application file for complete search history.

(56) References Cited

U.S. PATENT DOCUMENTS

| | | |
|---|---|---|
| 9,526,823 B2 | 12/2016 | Yoshioka |
| 2009/0186065 A1 | 7/2009 | Tillman et al. |
| 2011/0250287 A1 | 10/2011 | Bristow |
| 2013/0131423 A1 | 5/2013 | Wang et al. |
| 2014/0074007 A1 | 3/2014 | McNeil |
| 2015/0121808 A1 | 5/2015 | Gaitas et al. |
| 2015/0122737 A1 | 5/2015 | Gaitas |

FOREIGN PATENT DOCUMENTS

| | | |
|---|---|---|
| WO | 2006/006918 A1 | 1/2006 |
| WO | 2011/063940 A1 | 6/2011 |
| WO | 2011/123655 A1 | 10/2011 |
| WO | 2013/052951 A2 | 4/2013 |

OTHER PUBLICATIONS

Kim et al.: "Tumor self-seeding by circulating cancer cells", Cell, 2009, vol. 139(7), pp. 1315-1326.
Kim et al.: "A Novel Pathogen Capturing Device for Removal and Detection", Scientific Reports, 2017, 7(1), 5552, pp. 1-11.
Sheng et al.: "Capture, Release and Culture of Circulating Tumor Cells from Pancreatic Cancer Patients using an Enhanced Mixing Chip", Lab Chip., 2014, 1vol. 4(1), pp. 89-98.
Cheung et al.: "Adhesion dynamics of circulating tumor cells under shear flow in a bio-functionalized microchannel", Journal of Micromechanics and Microengineering, 2011, 21(5):054033.
Hong et al.: "Circulating tumor cell clusters: What we know and what we expect (Review)", International journal of oncology, 2016, vol. 49(6), pp. 2206-2216.
Ledebo et al.: "Haemodiafiltration-optimal efficiency and safety", NDT Plus, 2009, vol. 3(1), pp. 8-16.
Locatelli et al.:"The importance of convective transport", Kidney International Supplements, 2002, vol. 61 (80), pp. S115-S120.
Mitra et al.: "Technologies for deriving primary tumor cells for use in personalized cancer therapy", Trends in Biotechnology, 2013, vol. 31(6), pp. 347-354.
Guzman et al.: "A Two-Dimensional Affinity Capture and Separation Mini-Platform for the Isolation, Enrichment, and Quantification of Biomarkers and Its Potential Use for Liquid Biopsy", Biomedicines, 2020, 8, 255, pp. 1-37.
Tura et al.: "Identification of Circulating Melanoma Cells in Uveal Melanoma Patients by Dual-Marker Immunoenrichment", Investig. Ophthalmol. Vis. Sci., 2014, vol. 55, pp. 4395-4404.
Ribeiro-Samy et al.: "Fast and efficient microfluidic cell filter for isolation of circulating tumor cells from unprocessed whole blood of colorectal cancer patients", Sci. Rep., 2019, 9, 8032. pp. 1-12.
Kim et al.:"Extracorporeal Photo-Immunotherapy for Circulating Tumor Cells", PLoS ONE, 2015, 10, e0127219, pp. 1-9.
Edelman et al.: "The potential for reintroduction of tumor cells during intraoperative blood salvage: Reduction of risk with use of the RC-400 leukocyte depletion filter", Urology, 1996, vol. 47, pp. 179-181.
Frühauf et al.: "Filtration of malignant cells: Tumour cell depletion in an ex vivo model using a leukocyte adhesion filter", Perfusion, 2001, vol. 16, pp. 51-55.
Yu et al.: "Effective reduction of non-specific binding of blood cells in a microfluidic chip for isolation of rare cancer cells", Biomater. Sci., 2018, vol. 6, pp. 2871-2880.

* cited by examiner

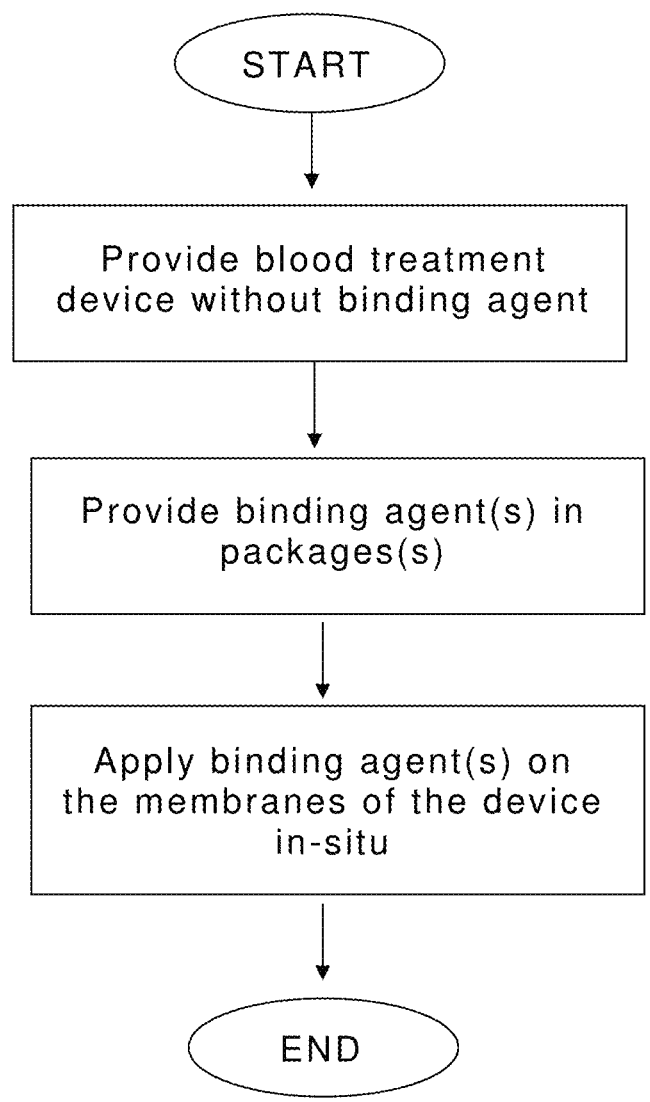
FIGURE 5.1

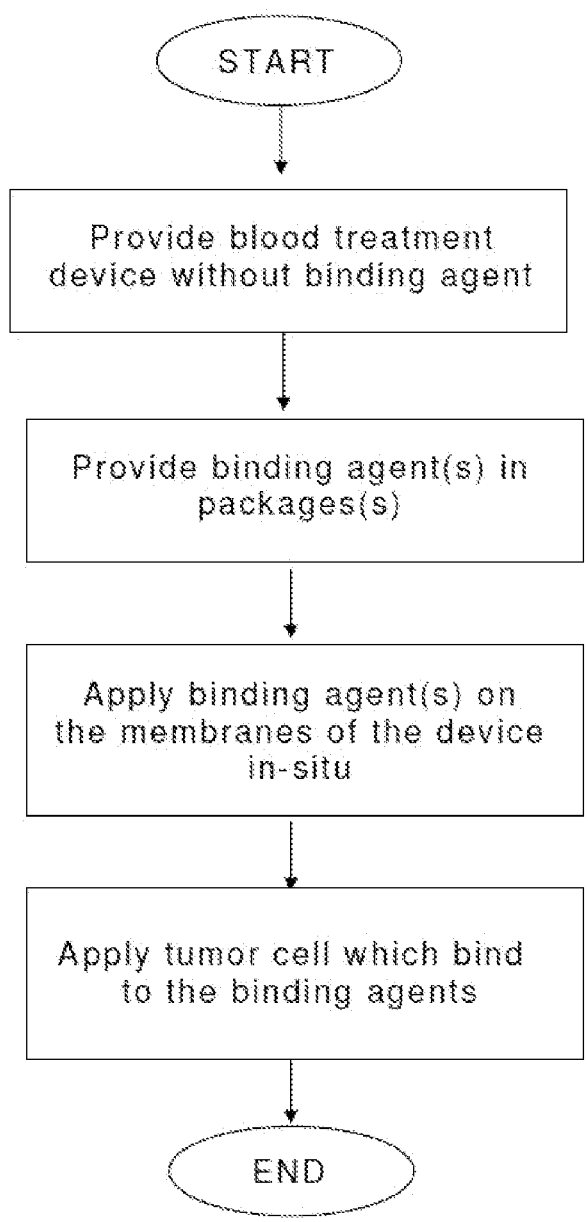
FIGURE 5.2

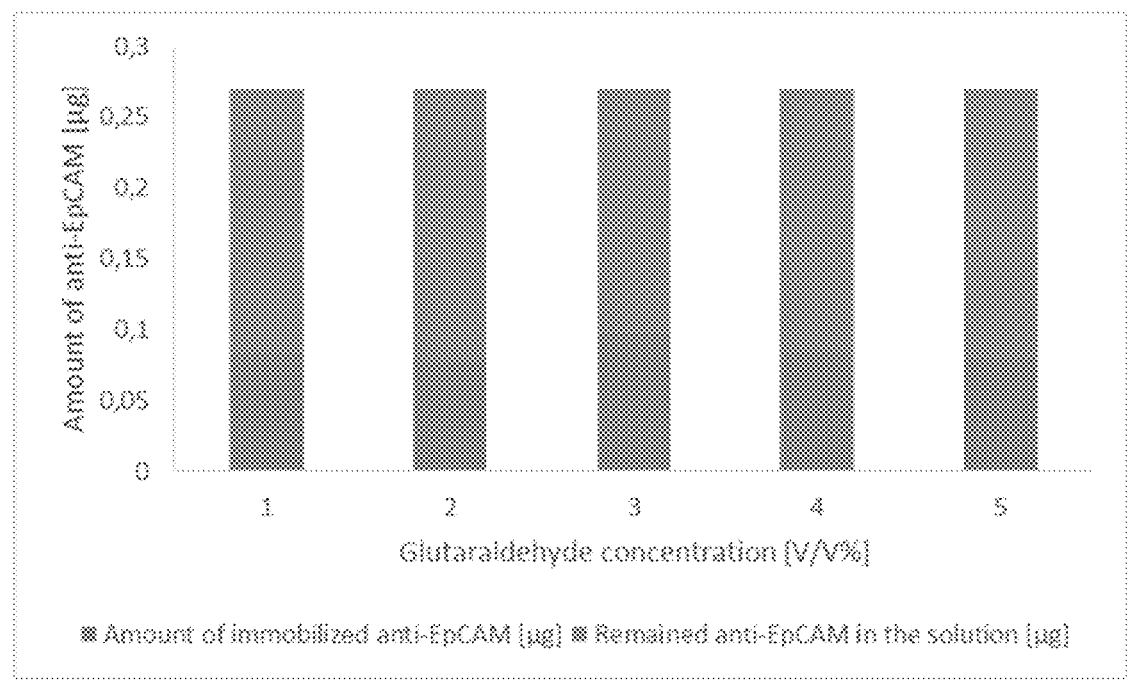
FIGURE 9
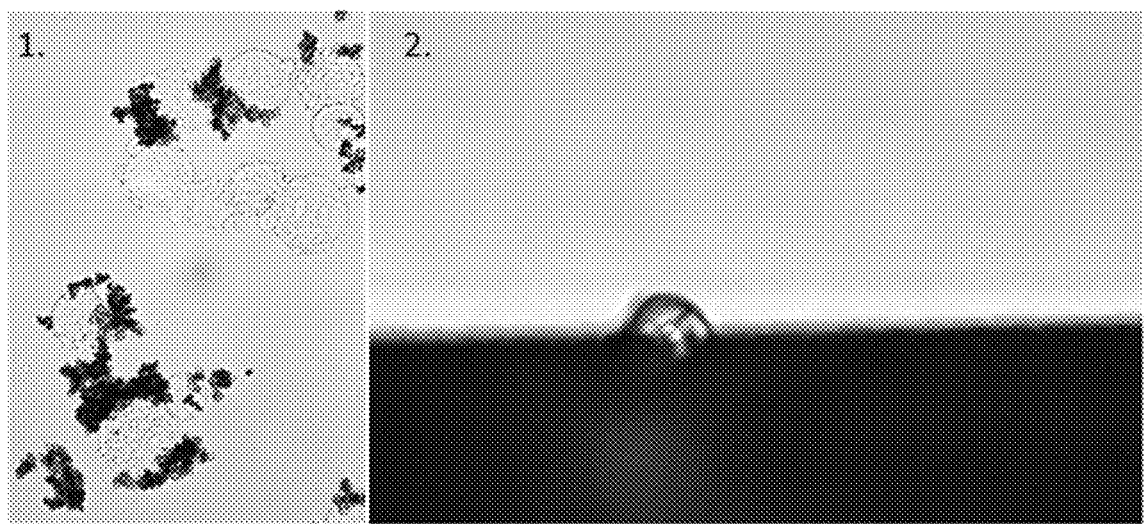
FIGURE 10.1          FIGURE 10.2

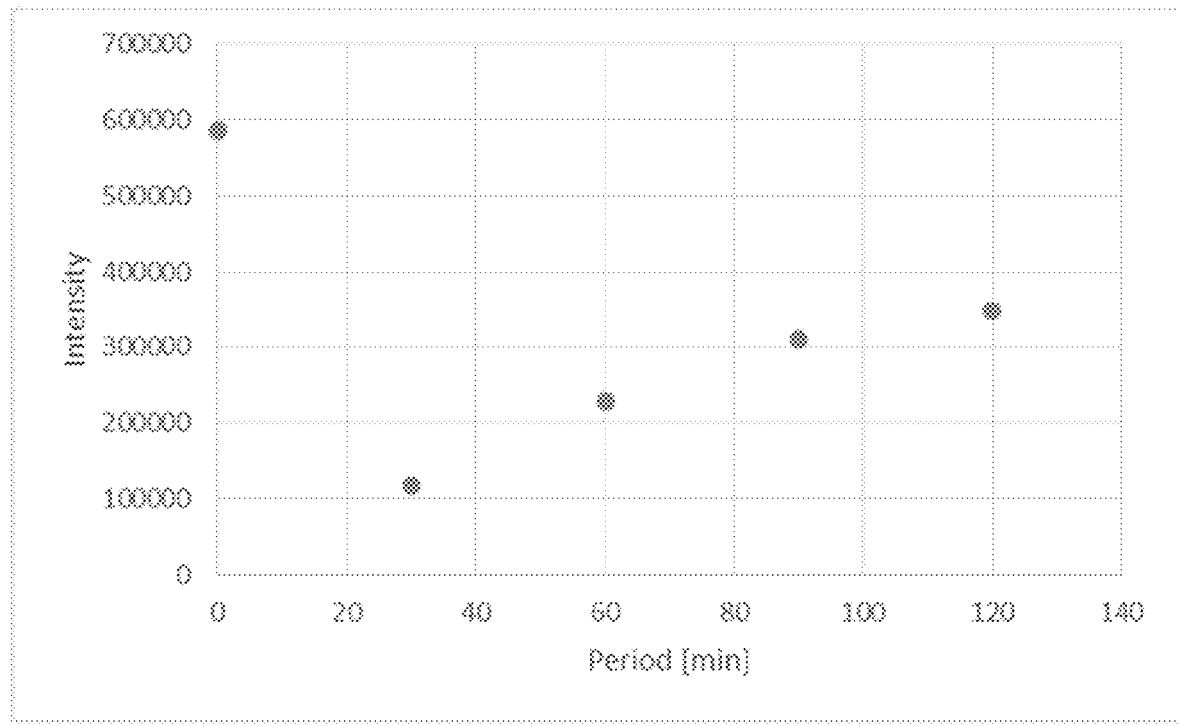
FIGURE 11
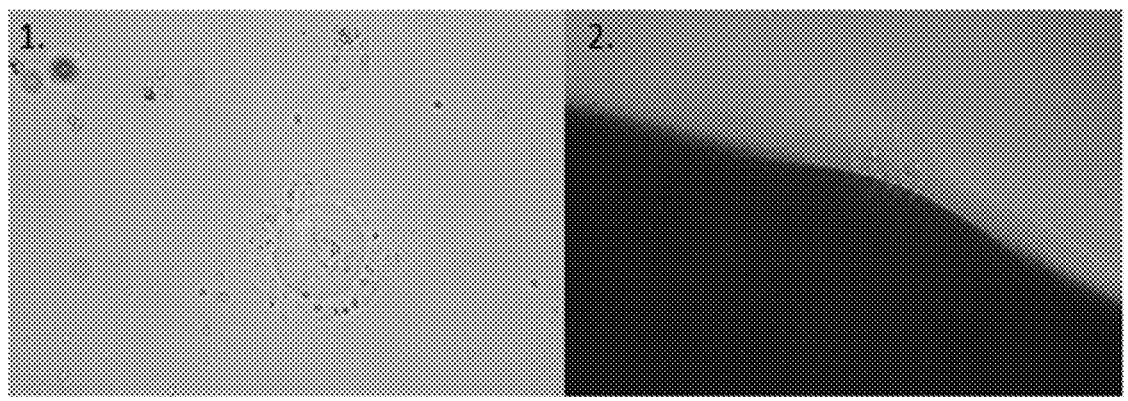
FIGURE 12.1          FIGURE 12.2

FLOW CAPTURE DEVICE AND METHOD FOR REMOVING CELLS FROM BLOOD

This is the national stage of International Application PCT/HU2017/050032 filed Jul. 28, 2017.

FIELD OF THE INVENTION

The current invention discloses a blood treating and/or purifying device for removing circulating pathogens, preferably pathogenic cells, more preferably circulating tumor cells from the blood of a patient, a method of producing such a device and method to treat cancer and other diseases caused by virus infection, bacterial infection and parasites infection as well as autoimmune disorders. The treatment is based on specific pathogen removal. The treatment method according to the present invention is intended to be used as therapeutic treatment, co-operational auxiliary treatment or a prevention method. The described method is an extracorporeal medical therapy, thus can be done also in a hemodialysis system. The current invention describes a device and an in-situ production method of preparing the device to remove CTC and other pathogens i.e. virus, bacteria or parasites from the bloodstream as well as to treat autoimmune diseases. The treatment is based on specific pathogen removal, optionally in parallel with hemodialysis of the unwanted substances.

BACKGROUND OF THE INVENTION

More than 90% of cancer deaths are due to metastases reported by the Viovy group in the Curie Institute [Autebert, J., et al., Microfluidic: an innovative tool for efficient cell sorting. Methods, 2012. 57(3): p. 297-307.] a well-known center of cancer research. While the entire tumorigenesis progress is not fully understood, it is strongly suggested that cells spreading from the primary tumor play a key role to initiate the metastatic process. Thus, in this patent application, circulating tumor cells (CTC) are defined as cells escaped from the primary tumor and circulating in the cardiovascular system. Tumor proliferation and invasion elevates the concentration of regular and irregular metabolites in the serum, which may alter and possibly inhibits the normal function of the entire human homoeostasis. One of the most abundant members of such tumor metabolites (also referred to as cytokines) is the tumor necrosis factor (TNF). Parallel removal of CTCs and their metabolites could alleviate the metastatic process and improve the patients' quality of life in conjunction with prolonged life expectancy.

Several attempts have been made to remove pathogens and in particular circulating cancer cells from blood stream of a patient.

Several authors applied extracorporeal deterioration of circulating cells For example, in U.S. Pat. No. 8,057,418 B2, [Korbling, M., et al., Devices and methods for extracorporeal ablation of circulating cells. 2011] an extracorporeal continuous flow pathway accesses the patient's blood to apply an external energy source to the blood at an ex vivo ablation device to result in the damage or death of the target cells. In U.S. Pat. No. 9,526,823 B2 [Yoshioka, S., Cell treatment device, cell treatment cartridge and body fluid treatment system. 2010] a complex cell treatment device is describe which allows cell dispersion liquid including cancer cells to pass therethrough to cause at least the cancer cells to be subjected to at least one of a physical, chemical action and a biologically activating action.

Some authors apply filtering out the cancer cells by some physical means like a membrane. For example, in US2014074007A1 [McNeil, Gary L, 2014] blood is separated with various filters.

GB2479536(A) [Lacy-Colson, Jon, Apheresis device and related methods 2011] describe in theory an apheresis filtration device for selective capture of circulating tumor cell from a patient's blood wherein the CTCs are captured to a solid support. However, no actual experiment has been carried out.

Gaitas, Angelo and Kim, Gwangseong [Chemically Modified Plastic Tube for High Volume Removal and Collection of Circulating Tumor Cells. PLoS ONE 10(7): e0133194. doi:10.1371/journal.pone.0133194] and in US2015121808A1 use a commercially available and chemically modified tube to selectively capture circulating tumor cells (CTCs) from the blood stream by immobilizing human anti-EpCAM antibodies on the tube's interior surface and were able to capture or entrap about 85% of cancer cells from suspension and 44% of cancer cells from spiked whole blood. The authors notify that the reduction in capture efficiency confirms the existing complications in CTC capturing in blood. They found that anti-coagulants can significantly interfere with the binding of EpCAM antibody to the targeted cancer cells.

BRIEF DESCRIPTION OF THE INVENTION

The invention is described briefly in the following numbered paragraphs:

1. An extracorporeal blood treatment device for removal of circulating pathogens, in particular pathogenic cells, preferably circulating tumor cells (CTCs), from blood of a mammalian patient, the device comprising:
    a house (10) having a blood inlet (12), blood outlet (14), a dialysate inlet (20) and a dialysate outlet (22),
    a filter unit arranged within the house (10), said filter unit being formed by a plurality of hollow fibers (16), each hollow fiber having a predetermined length and a wall in the form of a semi-permeable membrane (40) with a pore size of at most 1 micron;
    wherein said plurality of hollow fibers (16) provide a fluid communication between the blood inlet (12) and the blood outlet (14), and the space outside the hollow fibers (16) provides a separate fluid communication between the dialysate inlet (20) and the dialysate outlet (22),
    wherein the inner diameter of the hollow fibers (16) are in the range of 100 to 400 microns,
    wherein at least a part of the inner surfaces of the fiber membrane (40) adapted to contact the blood is coated with a binding agent for binding the pathogenic cells flowing in the blood stream; and
    wherein the inner diameter and the length of the hollow fibers (16) are dimensioned so that a linear flow velocity of $1.8 \times 10^{-5}$ m/s to $7 \times 10^{-5}$ m/s can be maintained for the blood along a substantial length of the hollow fibers (16) when a patient's blood is circulated in the device.

2. The device of preceding paragraph 1, wherein the binding agent is selected from a group consisting of proteins with specific binding site(s), in particular antibodies, glycoproteins, in particular mucins and/or lectins, oligonucleotide binding agents like aptamers, small binding molecules and ligands, in particular folic acid and any combinations of thereof.

3. The device of preceding paragraph 2, wherein the binding agent is an antibody or a binding fragment thereof or a biomolecule having a binding region of an antibody, said antibody being preferably a tumor specific antibody, in particular an antibody adapted to said mammal, more preferably an antibody selected from the group of anti-CD44 and anti-EpCAM antibodies.

4. The device of any of preceding paragraphs 1 to 3 wherein the membrane also comprises capture cells attached to the binding agents, said capture cells having a binding affinity to the circulating pathogens to bind them from the blood (preferably having a binding affinity higher or different affinity type (thereby possibly multiple binding) than the binding affinity of the binding agent to the capture cells) whereby the pathogens are captured by the capture cells; wherein preferably the pathogens are circulating tumor cells, the capture cells are capture tumor cells which are capable of forming multi-cell affinity conjugates (also referred to as clusters) with the circulating tumor cells.

5. The device of preceding paragraph 1, wherein the membrane of the hollow fibers is made of a biocompatible material wherein preferably said biocompatible material is selected from the group of polysulfone, resin of ethylene vinyl alcohol copolymer (EVOH), polyflux (PAES/PVP), polypropylene, polymethyl methacrylate, polynephron and polyether sulfone, or any suitable polymer or composite materials and any combination thereof and wherein preferably the binding is linked to the biocompatible material via a linker.

6. The device of preceding paragraph 1, wherein the pore size of the membrane of the hollow fibers ranges between 0.001 micron and 1 micron, preferably between 0.001 and 0.01 micron or between 0.01 and 0.1 micron or between 0.001 and 0.1 micron.

7. The device of preceding paragraph 1, wherein the house further comprises a fluid distributor arranged upstream the hollow fibers for uniformly distributing the blood stream over the hollow fibers.

8. The device of preceding paragraph 1, wherein the predetermined length of the hollow fibers is 0.5 to 50 cm, preferably 2 to 15 cm or 1 to 5 cm or 3 to 10 cm.

9. The device of preceding paragraph 1, wherein the device comprises 100 to 100000, preferably 1000 to 50 000, more preferably 10000 to 40000 parallel hollow fibers with an overall area of the semi-permeable membranes of at least 0.5 m$^2$, preferably 1 to 3 m$^2$.

10. A system (400) for operating an extracorporeal blood treatment device according to preceding paragraph 1, the system comprising:

a dialysis machine (410);

a dialysate container (450) for storing a dialysate to be used in a blood treatment process;

the blood treatment device (420) attached to said dialysis machine (410) and said dialysate container (450) via respective pipes (430, 431, 432, 433) for circulating the blood of a patient and a dialysate through the blood treatment device (420);

pipes (434, 432) for withdrawing and returning a patient's blood to/from said dialysis machine (410);

wherein said dialysis machine (410) comprises a control means (412) for controlling a linear flow velocity of the blood within the hollow fibers of the blood treatment device (420) within a range of $1.8 \times 10^5$ m/s to $7 \times 10^5$ m/s along a substantial length of the hollow fibers, thereby maintaining normal low shear conditions of blood in the hollow fibers to allow pathogenic cells to form clusters in the flowing blood and/or on the membrane surface of the hollow fibres once a pathogenic cell is bound by the binding agent.

11. An extracorporeal blood treatment method for removal of pathogens and thereby cleansing the blood, in particular pathogenic cells, preferably circulating cancer cells (CTCs) from blood of a mammalian patient, preferably a human patient, said method comprising:

leading (pumping) blood from the patient into a blood treating device according to preceding paragraph 1 or a blood treating device comprising/having a plurality of hollow fibers, each hollow fiber having a predetermined length and a wall in the form of a semi-permeable membrane with a pore size of at most 1 micron or a pore cut off value of at most 50 kDa, preferably 30 kDa (more preferably at most 20 kDa or 16 kDa);

providing a counter-current dialysate fluid flow in contact with the outer surface of the semi-permeable membrane of the hollow fibers, wherein the hydrostatic pressure inside the hollow fiber (in the blood) is higher than outside the hollow fiber (in the dialysate fluid)

wherein the inner diameter of the hollow fibers are in the range of 100 to 400 microns, wherein at least a part of the inner surfaces of the semi-permeable membrane contacting the blood is coated with a binding agent specific for binding CTCs or other pathogens flowing/present in the blood stream; and wherein the number, the inner diameter and/or the length of the hollow fibers are dimensioned so that a linear flow velocity of $1.8 \times 10^5$ m/s to $7 \times 10^5$ m/s of the blood is maintained along the longitudinal axis (or a substantial length of) the fibers (so that normal shear conditions of the blood is maintained) and convective flow is provided from the inside of the hollow fibers to the space outside the hollow fibers (e.g. due to the hydrostatic pressure difference between the blood (the inner space) and the dialysate (the outer space) and the pore size), said convective flow drives the cells to the membrane or assists/helps this lateral moving, whereby said pathogenic cells, preferably CTCs are bound by the binding agent, thereby cleansing the blood, leading the cleansed blood back to the patient.

12. The method according to preceding paragraph 11 wherein the device is a device according to any of preceding paragraphs 1 to 9, and wherein preferably normal low shear conditions of blood are provided in the hollow fibers.

13. The method according to preceding paragraph 11 or 12 wherein the method is selected from a haemodialysis method and the membrane in the device is a dialysis membrane, preferably a high flux haemodialysis method and the membrane is a high flux haemodialysis membrane, or a haemodiafiltration method and the membrane in the device is a haemodiafiltration membrane, wherein the blood comprises an anticoagulation agent, preferably heparin or other know anticoagulation agent.

14. The method according to any of preceding paragraphs 11 to 13 wherein the membrane also comprises capture cells attached to the binding agents, said capture cells having an affinity to the circulating pathogens whereby the pathogens are captured by the capture cells; wherein preferably the pathogens are circulating tumor cells, the capture cells are capture tumor cells which are capable of forming clusters (multi-cell affinity conjugates) with the circulating tumor cells wherein more preferably the capture tumor cell are derived from a tumor from said patient.

15. The method according to preceding paragraph 13 wherein the pathogenic cells are CTCs and CTCs form clusters in the blood and/or when bound by the binding agent (wherein preferably said clusters consist of at least 2, preferably 2 to 50, more preferably 3 to 20 or 3 to 10 cells).

16. The method according to any of preceding paragraphs 11 to 15 wherein the binding agent is selected from a group of binding agents consisting of proteins with specific binding site(s), in particular antibodies; glycoproteins, in particular mucins and/or lectins; oligonucleotide binding agents like aptamers, small binding molecules and ligands, in particular folic acid and any combinations of thereof.

17. The method according to preceding paragraph 16 wherein the binding agent is a protein having a binding site specific for the pathogenic cell and wherein non-specific binding sites are covered by an inert protein, in particular albumin.

18. The method of any of preceding paragraphs 16 to 17, wherein binding agent is an antibody or a binding fragment thereof or a biomolecule having a binding region of an antibody, said antibody being preferably a tumor specific antibody, in particular an antibody adapted to said mammal, preferably an antibody selected from the group of CD44 and EpCAM antibodies.

19. The method according to any of preceding paragraphs 11 to 18 wherein the pathogenic cells are CTCs and patient is selected from the group consisting of
 a patient with cancer,
 a patient after operation for removing tumor,
 a patient in need of prevention of tumor metastasis,
 a patient under chemotherapy or radiation therapy,
 a patient during surgery i,e, during the removal of the tumor and surrounding tissue.

20. The method of preceding paragraph 19 wherein the mammalian patient is a human and the binding agent is a tumor specific antibody. The antibody may be humanized or adapted to a mammal or have an artificial scaffold.

21. A semi-permeable membrane for use in the extracorporeal blood cleansing method for removal of circulating pathogens, in particular pathogenic cells, preferably circulating tumor cells (CTCs) from blood of a mammalian patient, preferably a human patient, according to any of preceding paragraphs 11 to 20; said membrane
 having a pore size of at most 1 micron or a pore cut off value of at most 50 kDa, preferably 30 kDa (preferably at most 20 kDa or 16 kDa);
 the surface of the semi-permeable membrane contacting the blood is coated with a binding agent specific for binding of the pathogenic cells, preferably CTCs present in the blood stream, preferably in a device according to any of preceding paragraphs 1 to 9.

22. The semi-permeable membrane for use according to preceding paragraph 21 wherein said semi-permeable membrane is a haemodialysis membrane, preferably a high-flux haemodialysis membrane, wherein preferably the pore size of the membrane of the hollow fibers ranges between 0.001 micron and 1 micron, preferred ranges see in par. 6.

23. The semi-permeable membrane for use according to any of preceding paragraphs 21 to 22, wherein the membrane also comprises capture cells attached to the binding agents, said capture cells having an affinity to the circulating pathogens whereby the pathogens are captured by the capture cells; wherein preferably the pathogens are circulating tumor cells,
 the capture cells are capture tumor cells, which are capable of forming clusters (multi-cell affinity conjugates) with the circulating tumor cells wherein more preferably the capture tumor cells are derived from a tumor from said patient.

24. The semi-permeable membrane for use according to any of preceding paragraphs 21 to 23, wherein said membrane is made of a biocompatible material preferably selected from the group of polysulfone, resin of ethylene vinyl alcohol copolymer (EVOH), polyflux (PAES/PVP), polypropylene, polymethyl methacrylate, polynephron and polyether sulfone, and any suitable material or any combination thereof.

25. The semi-permeable membrane for use according to any of preceding paragraphs 21 to 24 wherein the binding agent is selected from a group of binding agents consisting of proteins with specific binding site(s), in particular antibodies; glycoproteins, in particular mucins and/or lectins; oligonucleotide binding agents like aptamers, small binding molecules and ligands, in particular folic acid and any combinations of thereof.

27. The semi-permeable membrane for use according to any of preceding paragraphs 21 to 26 wherein the binding agent is a protein having a binding site specific for the pathogenic cell and wherein non-specific binding sites are covered by an inert protein, in particular albumin.

28. The semi-permeable membrane for use according to preceding paragraph 25 or 27, wherein binding agent is an antibody or a binding fragment thereof or a biomolecule having a binding region of an antibody, said antibody being preferably a tumor specific antibody, preferably an antibody adapted to said mammal, preferably an antibody selected from the group of anti-EpCAM, including CD44 and EpCAM antibodies.

29. The semi-permeable membrane for use according to any of preceding paragraphs 21 to 28 wherein the pathogenic cells are CTCs and the patient is selected from the group consisting of
 a patient with cancer,
 a patient after operation for removing tumor,
 a patient in need of prevention of tumor metastasis,
 a patient under chemotherapy or radiation therapy,
 a patient during surgery i,e, during the removal of the tumor and surrounding tissue.

30. The semi-permeable membrane for use according to preceding paragraph 29 wherein the mammalian patient is a human and preferably the binding agent is a tumor specific antibody. The antibody may be adapted to the mammal or may have an artificial scaffold.

31. A method of in-situ production of an extracorporeal blood treatment device, the method comprising the steps of:
 providing a sterile blood treatment device as defined in any of preceding paragraphs 1 to 9 without binding agent;
 providing a predetermined amount of a specific binding agent or various binding agents in the form of one or more solutions, each solution being made at an appropriate concentration and stored in a package;
 at the location of a blood treatment process, applying the solution of the binding agent, or subsequently applying multiple solutions of different binding agents on least a part of the overall membrane surface of the hollow fibers of the blood treatment device binding agent.

32. The method of preceding paragraph 31, wherein the capturing agent is applied on the membrane surfaces by circulating the solution(s) of the binding agent(s) through the hollow fibers of the blood treatment device by means of a dialyser machine.

33. The method of preceding paragraph 31 or 32, comprising using a haemodialysis cartridge as the blood treatment device.

34. The method of preceding paragraph 31 or 32, further comprising adding capture cells to the binding agents, whereby covering the binding sites of the binding agents with capture cells wherein said capture cells having an affinity to the circulating pathogens whereby the pathogens are captured by the capture cells; wherein preferably the pathogens are circulating tumor cells,
the capture cells are capture tumor cells which are capable of forming clusters (multi-cell affinity conjugates) with the circulating tumor cells wherein more preferably the capture tumor cell are derived from a tumor from said patient.

35. The method of preceding paragraph 34, wherein the capture cells are primary tumor cells derived from a tumor from said patient.

36. The method of any of preceding paragraphs 34 to 35, further comprising adding an inert protein to the membrane whereby the non-specific binding sites are covered by an inert protein, in particular albumin.

37. The method of any of preceding paragraphs 34 to 36 wherein the capture cells and the serum albumin is provided by incubating the membrane in the blood of said patient to allow binding the capture cells to the binding sites of the binding agents and binding of serum albumin to non-specific binding sites.

38. Use of a kit in a method of any of preceding paragraphs 31 to 37, said kit comprising a predetermined amount of a specific binding agent or various binding agents as defined in any of the previous numbered paragraphs, in the form of one or more solutions, each solution being made at an appropriate concentration and stored in a package;

and optionally a predetermined amount of a linker agent useful to bind the binding agent to the semi-permeable membrane.

BRIEF DESCRIPTION OF THE DRAWINGS

FIG. 5 illustrates a flow diagram of the method of in-situ production of the extracorporeal blood treatment device, in accordance with the present invention. FIG. 5.1 illustrates a chart when the process ends with the application of binding agents to the membrane whereas FIG. 5.2 illustrates a chart when a lawn of capturing cells is administered and bound to the binding agents.

FIG. 9 illustrates the setting the glutaraldehyde concentration for anti-EpCAM immobilization FIG. 10 shows a proof of concept experiment indicating that anti-EpCAM can capture CTCs In the experiment shown on FIG. 10.1 magnetic beads were used to immobilize anti-EpCAM. The beads were used to prove that anti-EpCAM antibody binds the CTCs (modeled by Colon carcinoma cells HT29) under flow conditions. It is shown that CTCs form clusters, i.e. the CTC bound binds further CTCs with a high specificity. In the experiment shown on FIG. 10 2 immobilized anti-EpCAM binds CTC (colon HT29 cells) an polysulfone membrane of a hollow fiber.

FIG. 11 shows an experiment proving the applicability of 2-picoline borane in 5% EtOH for anti-EpCAM immobilization FIG. 12 shows an experiment indicating that folic acid can capture CTCs In the experiment shown on FIG. 12.1 folic acid was immobilized on aminated magnetic beads according to the polysulfone immobilization recipe to prove folic acid bound CTCs modeled by colon carcinoma HT29 cells. On FIG. 12.2 folic acid was immobilized on polysulfone surface, CTC was bound by folic acid and the CTCs (colon HT29) were captured.

DETAILED DESCRIPTION OF THE INVENTION AND THE PREFERRED EMBODIMENT

Figure 1:
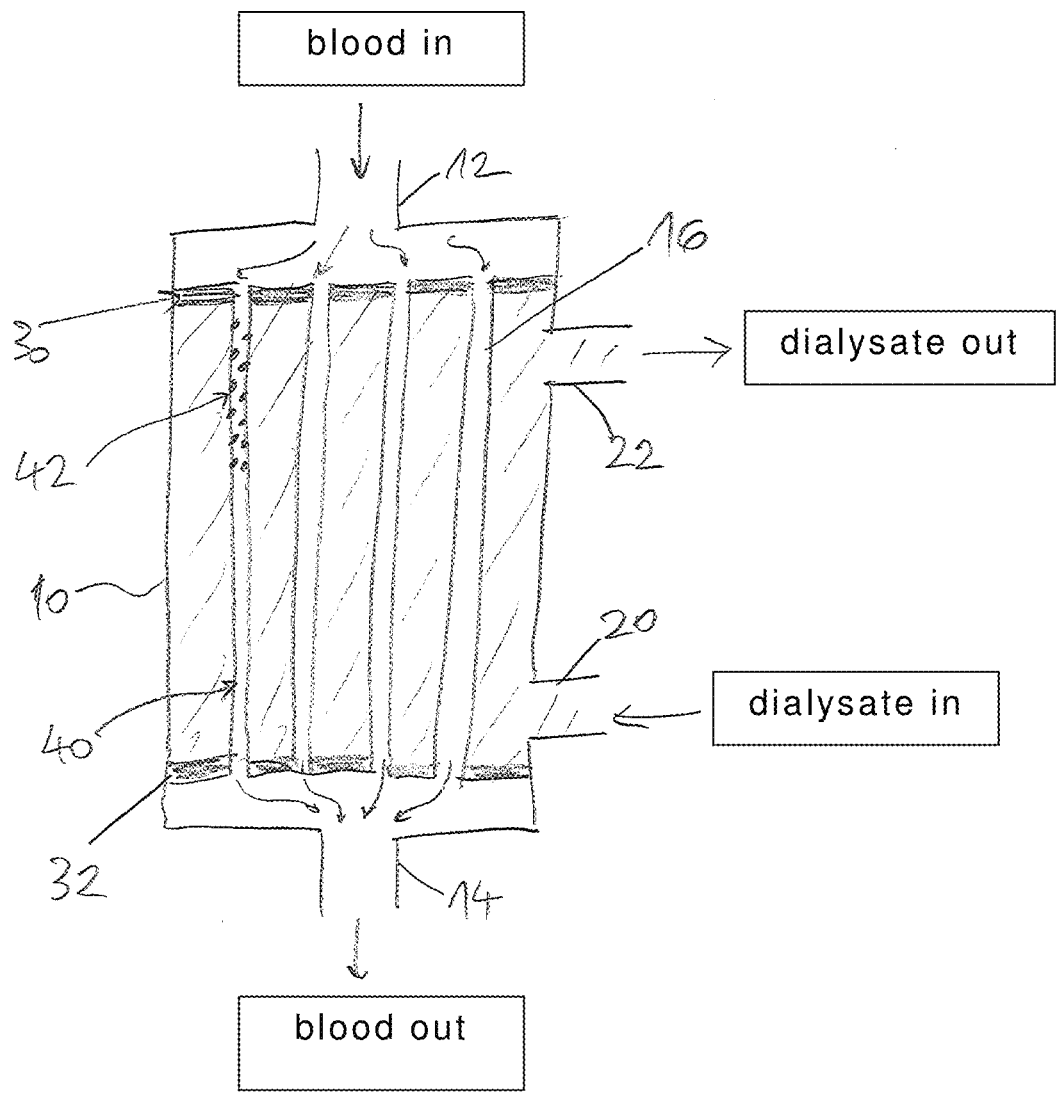
FIG. 1 schematically illustrates the extracorporeal blood treatment device according to the invention in a cross-sectional view with a fluid distributor.

The current invention discloses a method and a device intended to use as functional part of an extracorporeal system in order to at least partly or completely remove the CTCs and other pathogens from the cardiovascular system of human beings or mammals (pets). Preferably, the removal of CTCs and other pathogens may be carried out in parallel with hemodialysis of unwanted possibly harmful substances present in the blood stream due to an actual disease or diseases of a patient. Pathogens include but not limited to CTCs (including solid tumor originated cells as well as leukemia), viruses, bacteria, malignant antibodies due to autoimmune diseases, parasites, and toxins. Extracorporeal medical therapy is a procedure in which blood is taken from a patient's circulation to conduct the process described herein and then returned to the circulation after treatment. Blood is withdrawn from the patient's artery and returned to the vein. For the time being, the most common extracorporeal therapy is hemodialysis to treat renal failure.

The present inventors have recognized that pathogen, in particular pathogenic cell, preferably circulating tumor cells (CTCs) can effectively removed from the blood of a patient in an extracorporeal method by using a novel derivatized membrane having a pore size typical in haemodialysis, preferably in high flux heamodialysis, wherein the hydrostatic pressure in the blood flow side of the membrane is higher than in the other side, thereby convective flow through the pores occurs; the pathogens contact the inner (blood) side of the membrane which comprises binding agents specific to the pathogens and thereby binds them in a stable manner so as to remove them from the blood flow, whereas the pressure and flow properties similar to those in the blood vessels are maintained so that avoid high shear conditions.

In a preferred embodiment not only pressure and flow conditions of hemodialysis are maintained but a device, such as a cartridge for hemodialysis is used. This is not obligatory under the present invention but has several advantages. Hemodialysis is a usual procedure in many patient centers, in particular cancer centers must often consider kidney failures, often chronic kidney diseases and this kind of treatment is usual in such cases. Thus, for example the inventive method can be integrated into existing hemodialysis protocol or the existing protocol can be adapted easily to the inventive method.

In a preferred embodiment of the invention, the removal of CTCs or other pathogens carried out in parallel with hemodialysis of unwanted possibly harmful substances present in the blood stream due to an actual disease or diseases of a patient. This unique synergy of hemodialysis and CTC entrapping resulted in improved capturing efficiency.

However, the setting usual in hemodialysis provides additional advantage as well. Basically, hemodialyzer cartridges contain semi-permeable membranes, which can be classified into two distinct groups: low-flux and high-flux dialyzers. Low-flux membranes have moderate permeability for water, i.e. hydraulic permeability (KUF) is typically around 15 [mL/hr/mmHg (mL/hr/kPa)], while high-flux membranes are capable of removing moderate-sized molecules between 10 to 16 kiloDalton (normally have KUF value around 70 [mL/hr/mmHg (mL/hr/kPa)] in parallel with increased flux for water.

Generally, in case of low-flux membranes the governing transport mechanism is the diffusion. On the other hand, in high-flux dialyzers convective mass transport plays major role while the effect of diffusion is less important. Since the higher the molecular mass the lower its diffusion constant thus convective transport is more significant in the higher molecular weight range i.e. in the range of cytokines. The convective transport act towards the surface normal direction. Surprisingly, according to a preferred embodiment the present inventors have recognized that by applying the flow conditions described in section "Flow conditions" this convective mass transport is maintainable, which drags the CTCs towards the hollow fibers inner surface which resulted in enhanced cell capture efficiency.

In an alternative method hemodiafiltration can be applied in the present invention.

As an additional advantage high-flux membranes are appropriate to remove certain toxic factors and metabolites which may play role in cancer or cancer metastases. For example, tumor necrosis factor (TNF) is one of the most abundant tumor metabolites i.e. toxic unwanted substances. Certain forms of TNFα, a subgroup of TNF, weighs around 16 kD, thus can be removed by diffusion and ultrafiltration mechanisms. Immobilization of the immuno-affinity capture agents (i.e., activation) does not affect the hemopurification ability of the membrane, thus the current invention inherently serves as the combination of blood purification and treatment processes, i.e., simultaneously flow-capturing pathogens by immuno-affinity while also supporting hemofiltration.

Anticoagulation

Anticoagulation is an important component of the dialysis prescription [Roy, Anupam and Kalra, Vikram, Anticoagulation In Haemodialysis. JIMSA April-June 2012 Vol. 25 No. 2]. Roy and Kalra summarize mechanisms of clotting and explain that clotting in the extracorporeal circuit occurs as a result of activation of platelets and coagulation cascade. Interaction of plasma with the dialyser membrane is determined by "various factors like slow blood flow rate, high ultrafiltration rate, high haematocrit, access recirculation, intradialytic blood product transfusion etc also contribute to thrombogenesis.

Heparin is the most commonly used anticoagulant. Thus, application of some form of heparin appears to necessary in hemodialysis procedure, in particular at slow flow rates which are preferred in the present invention; whereas Gaitas and Kim (PLOS One 2015, see above) advised that anticoagulants are deleterious in a method for capturing CTCs from blood in tubes and thus taught away from using a method like hemodialysis or similar conditions wherein anticoagulants are unavoidable.

Figure 13:
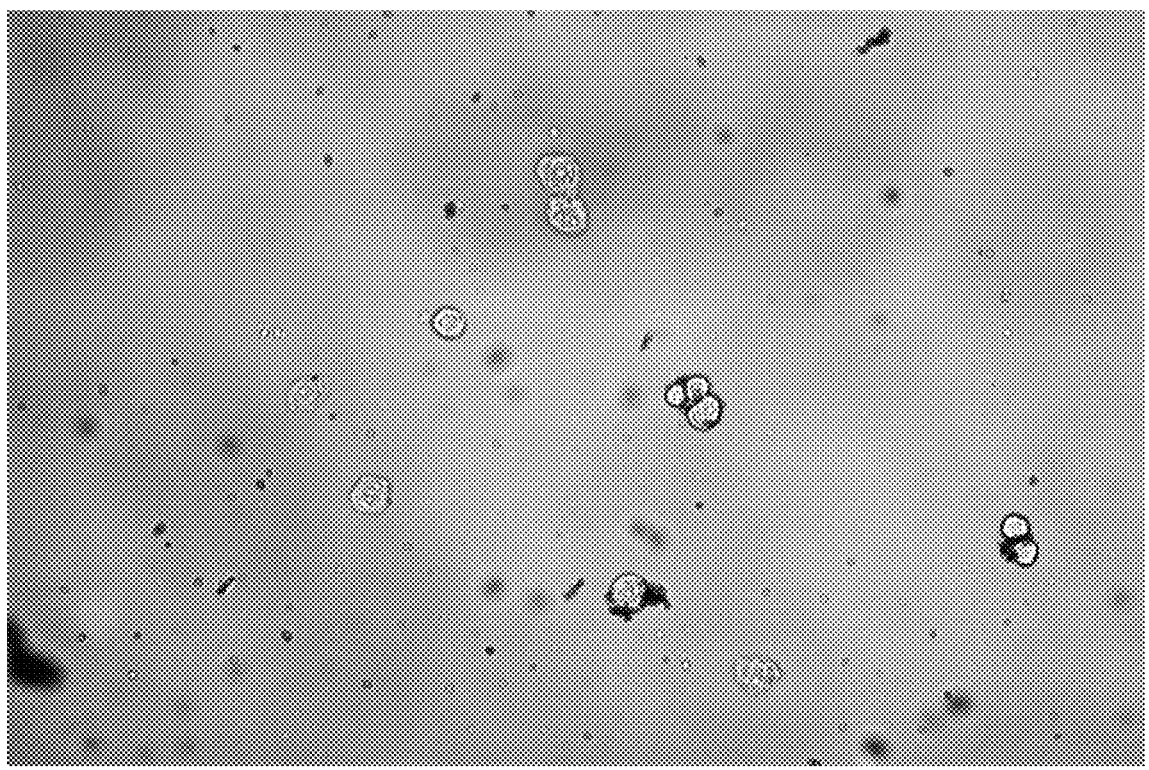
FIG. 13 is a picture showing clustering of CTCs in heparin containing blood flow.

However, the present inventors have surprisingly found in the present inventive method heparin is not prevents an efficient removal of CTCs. Moreover, FIG. 13 illustrates that cell-to-cell interaction occurs even in heparin containing blood stream.

Flow Conditions and Cartridges

A typical adhesion force between a single binding agent and any pathogens is 110±41 nN measured by atomic force microscopy [Meng, J., et al., Adhesion between peptides/antibodies and breast cancer cells. Journal of Applied Physics, 2010. 107(11): p. 114301.]. Due to the blood flow in the hollow fibers, a shear stress is acting on the immobilized cells or pathogens. In order to keep the shear stress lower than the threshold value of critical flow velocity (CFV), which causes the captured pathogens to break off and return into the blood stream, the maximum velocity applicable in a hollow fiber in one example is $4 \times 10^{-5}$ m/s using 200 nm inner diameter tubing and assuming a 15 µm diameter tumor cell with binding sites equal or less than 10. In practice, the linear flow velocity may be e.g $1.8 \times 10^{-5}$ m/s to $7 \times 10^{-5}$ m/s or $1.8 \times 10^{-5}$ m/s to $4 \times 10^{-5}$ m/s $1.2 \times 10^{-5}$ m/s to $3 \times 10^{-5}$ m/s $1.8 \times 10^{5}$ m/s to $3 \times 10^{-5}$ m/s of the blood is maintained.

Appropriate flow rate is ensured by cartridge design and/or by the pumping speed which may be driven by a software, eg. a modified adapted hemodialysis software.

Current commercially available hemodialysis cartridges are designed and engineered to ensure high filtration flux. The cartridge is a tube in tube design, where the blood and the hemodialysis solution are separated by high surface to volume ratio membranes. High surface area is achieved by the use of thousands of hollow fibers, enclosed in the shell (housing). In this embodiment linear flow velocity in the fibers is limited considering the shear stress to make it suitable for blood components. Prior art cartridge design also takes treatment time into consideration. A typical hemodialysis takes around 4 hours, meaning that the whole blood of an average 80 kg person is filtered through the membrane 10-20 times depending on the treatment. This results in the blood flow rate of 200-500 mL/min in the entire cartridge.

However, removal of pathogens by immuno-affinity techniques requires thorough considerations regarding the linear flow velocity in the hollow fibers. The formed shear stress on the captured pathogens is a direct function of the linear flow velocity. In order to avoid possible removal of the captured immobilized target molecules or cells from the solid support, the linear velocity should be optimized also considering possible shear stress based leaking of the binding agents to enter the blood stream.

The present inventors have recognized that when a cancer cell is captured and bound to the membrane of a hollow fiber, further cancer cells tend to attach to the first captured cell in a similar way that takes place during a metastatic process. It appears based on the present inventors" observations that typically a few or usually at most a few tens of cells attach to each other. As the diameter of a cluster formed by a number of captured cancer cells, even a few tens of cells, is substantially larger than the diameter of a single cell bound to the membrane of the hollow fiber, the cluster is subject to the impacts of many other substances flowing in the blood stream at a much higher chance, which may result in physically damaging the superficial cells of such clusters, which in most cases, is fatal to those cells. The parts of the damaged and mostly dead cancer cell(s) will be then carried away by the blood stream. However, these impaired cell do not form metastasis any more. Due to this phenomenon, the primary aim of removing the (vital) CTCs or other pathogenic cells from the blood is also achieved.

Cell to Cell Binding and it Utilization in the Present Invention

Pathogen removal, described in this patent application, comprises specific binding between specific parts or the entire pathogen and the capture agent. Capture agents include but not limited to antibodies (e.g. cancer antibodies, like an anti-EpCAM antibody), folic acid, aptamers, mucins, lectins and any combinations of them.

Furthermore, the present inventors have recognized that utilization of cell to cell (c2c) adhesion (i.e., clustering) is also considered to expand the capabilities of the flow-capture technology for personalized medicine. c2c approach benefits from the well-known fact that CTCs can colonize their tumors of origin [Kim, M. Y., et al., Tumor self-seeding by circulating cancer cells. Cell, 2009. 139(7): p. 1315-26.]. This c2c interaction is utilizing an inherent personalized cancer therapy, since the patient's own CTCs have specific affinity to preferably bind each other and form cell clusters.

Thus, the present invention concerns two types of CTC removal:

In an embodiment CTCs are flow-captured utilizing said cartridge with capture agents or combinations of several of them.

In a further embodiment (indirect mode) the activated cartridge, i.e. the cartridge which comprises the binding agents, is loaded in a further step with tumor cells.

In a variant of this embodiment tumor cell are in the form of a cell suspension containing patient's own tumor cells originated from the known tumor of the patient, wherein the cells would serve as personalized capture agent. The tumor may be obtained by surgical removal of the tumor or from a tumor biopsy.

Methods for preparing or deriving primary tumor cells are well known in the art [see e.g. Mitra A. et al. Technologies for deriving primary tumor cells for use in personalized cancer therapy. Trends Biotechnol. 2013 31(6): 347-354, incorporated herein by reference]. Also in general, techniques for isolating cells and growing them in culture are well known in the art [Alberts B, Johnson A, Lewis J, et al. Molecular Biology of the Cell. 4th edition. New York: Garland Science; 2002. Isolating Cells and Growing Them in Culture. Available from: https://www.ncbi.nlm.nih.gov/books/NBK26851/]. Tumor cell isolation kits are available e.g. from Miltenyi Biotech. Procedures in Cancer Medicine are also well know for a skilled person [see e.g. Kufe, Donald W et al. (Eds) Holland-Frei Cancer Medicine, 6th edition Hamilton (ON): BC Decker; 2003. ISBN-10: 1-55009-213-8].

Furthermore, cells can origin from artificial cancer cell lines or other suitable sources. It is advisable if the original source of the cancer cell line is a similar type of cancer to the treated in the patient. Typically, highly metastatic cancers are treated by the method of the invention. A typical example is melanoma. In this case a melanoma cell line (like A375 Cell Line human (Sigma-Aldrich and ECACC) or human skin melanoma (HT168-M1/9), in short M1/9 melanoma cell line) may be appropriate for use in the present invention. Other example may be colon cancer cells like human colon adenocarcinoma cell line HT29.

In these embodiments the capture agents are in fact flow-capture tumor cells, which form a so called primary layer (or lawn) of tumor cells serving as nucleation centers for cell cluster formation. This cell-to-cell (c2c) approach improves and personalizes the CTC removal efficiency since the patient's own cells have more specific affinity to bind each other, even can bind mutated CTCs, which could not be ablated using general purpose or cancer specific antibodies or other binding agents.

In a further preferred variant of this embodiment the patient's own blood which is applied on the cartridge of the device and incubated till the CTCs are bond to specific binding sites and non-specific binding sites are covered by autologous serum albumin.

The current patent application describes a novel pathogen removal process utilizing the combination of different capture agents. Activation of said cartridge with combination of multiple capture agents can be carried out in two ways: 1) by means of consecutive reaction schemes when the different capture agents (two or more) require altering immobilization chemistry, i.e. different surface pretreatment and/or different functional groups. In one example, anti-EpCAM is immobilized on the surface of the polysulfone hollow fiber membrane using chemistry descripted above then folic acid is immobilized in order to maximize removal capacity and efficiency; 2) simultaneous activation is suitable for capture agents having identical immobilization chemistry. In one example anti-EpCAM is immobilized as general purpose binding agent and CD44 is used for improved specificity and capacity. Since both antibodies can be immobilized using the same reaction schemes, they can be immobilized simultaneously. In one example polysulfone fibers are exposed to 15-30 mg/mL anti-EpCAM and CD44 and N-ethyl-N'-(3-dimethylaminopropyl)carbodiimide hydrochloride (EDC) solution (EDC is the media for antibodies) for 1-2 hours at room temperature. Ratio of anti-EpCAM and CD44 concentrations controls the composition of the activated surface coverage.

In an alternative embodiment, a combined cartridge (i.e., cartridge with two or more types of capture agents) can be manufactured using different types of hollow fibers, which are previously activated separately with certain capture agents. With this approach, the ratio between the number of different types of fibers controls the apparent ratio of the activated surface coverage.

Devices

To be able to use typical treatment conditions and similar time duration to normal hemodialysis during CTC or other pathogen removal treatment, a new blood treatment device (cartridge) has been designed.

As shown in FIG. 1, the blood treatment device comprises a house 10 provided with a blood inlet 12 and a blood outlet 14, which are in fluid communication with each other. Within the inner space of the house 10, a filter unit formed by a plurality of hollow fibers 16 is arranged in a way that the entire amount of the blood stream, which is fed into the device is forced to flow through the hollow fibers 16. To this end the hollow fibers 16 are mounted to a header 30, 32 at their both ends, said headers 30, 32 being sealingly attached to the inner side of the wall of the house 10.

The wall of the hollow fibers 16 is formed by a semipermeable membrane 40 with a pore size of at most 1 micron, preferably ranging from 0.001 micron to 0.01 micron. The hollow fibers 16 may be made of polysulfone, resin of ethylene vinyl alcohol copolymer (EVOH), polyflux (PAES/PVP), polypropylene, polymethyl methacrylate, polynephron and polyether sulfone or other suitable materials and can be coated with any suitable material. The thickness of the membrane wall is typically 6 to 30 microns. The overall membrane surface area of the whole filter unit typically ranges from 0.5-3 $m^2$, preferably 0.75 $m^2$ to 2 $m^2$ for an efficient continuous blood treatment process. As a coating material for example PEI (polyethylenimine) can be used, which is one of the most preferred coating material.

The device further comprises an inlet 20 and an outlet 22 for the dialysate to be used in the blood treatment process for extracting the unwanted substances from the blood stream flowing through the hollow fibers 16 of the filter unit.

The membrane 40 of the hollow fibers 16 provides an adsorptive surface for binding and/or capturing CTCs or other pathogenic cells from the blood stream flowing through the hollow fibers 16. The membrane surfaces of the filter unit are at least partly coated with a specific binding agent 42 or a mixture of various binding agents for biding the CTCs or other pathogenic cells flowing within the blood stream while the blood is circulated through the filter of the device during a blood treatment process. The entire device is preferably made of a bio-compatible material. The adsorption surface of the filter unit is coated with any combination of the binding agent(s), which will be specified later.

Figure 2:
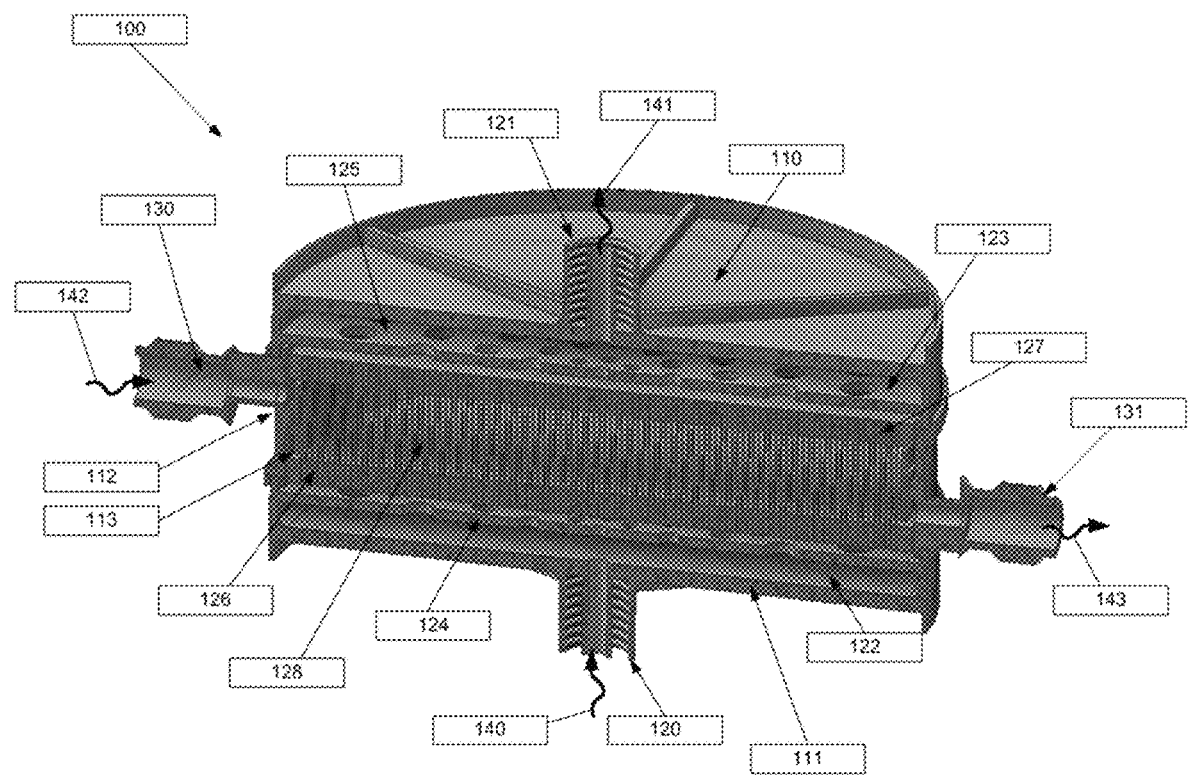
FIG. 2 is a cross-section of a multifunctional blood treatment device according to a preferred embodiment of the invention.

FIG. 2 shows a preferred embodiment of the blood treatment device according to the present invention. This device 100 may be used in a dialyzer system a dialyser cartridge for a combined treatment of the blood with respect to both hemodialysis and removal of CTCs or other pathogenic cells. The blood treatment device 100 has a cartridge body 112 comprising an arterial head space 122 and a venous head space 123, separated by a filtrate space 113. Blood flows into the device 100 through an inlet port 120 and flows out through an outlet port 121 placed in header cups 110 and 111 in the direction indicated by the curved arrows 140 and 141. Since blood is considered as a non-Newtonian fluid, the blood stream is uniformly spread by the built in fluid distributors 124 and 125 to ensure homogeneous particle distribution over the entire cross-section of the device 100 perpendicular to the flow direction of the blood within the cartridge between the headers 126 and 127 of the filter space.

To ensure bidirectional flow capability, fluid distributors 124, 125 are arranged at both ends of the device 100. The headers 126 and 127 arranged at the arterial and venous sides, respectively, are used to hold a plurality of hollow fibers 128 embedded, for example, in a resin. The dialysate is fed into the cartridge through an inlet port 130, it is circulated through the free space within the cartridge body 112 and discharged through an outlet port 131. The flow direction of the dialysate is shown by arrows 142 and 143. The device 100 preferably contains preferably contains 100 to 100000, preferably 1000 to 50 000, more preferably 10000 to 40000 hollow fibers.

The device 100 is manufactured by using biocompatible materials, which can be subjected to a sterilization process without changing any chemical, biochemical or structural feature of the device 100. For this purpose polycarbonate, polypropylene and poly(vinyl chloride) can be used as cartridge material. Preferably, polycarbonate is used.

The binding agents, which are used to bind the CTCs or other pathogenic cells on the membrane surface of the hollow fibers 128 are applied onto the inner surface of the hollow fibers 128 that is in direct contact with the blood stream during the blood treatment process. In this embodiment, the wall of the hollow fibers 128 are formed as semi-permeable membranes to allow removal of unwanted substances or cells from the blood stream. It is preferred that the internal diameter of the hollow fibers 128 ranges between 100 to 400 micrometers. This relatively small diameter range of the hollow fibers 128 may have the following benefits.

The fibers 128 may be made of polysulfone, resin of ethylene vinyl alcohol copolymer (EVOH), polyflux (PAES/PVP), polypropylene, polymethyl methacrylate, polynephron and polyether sulfone or other suitable materials and can be coated with any suitable material, for example PEI (polyethylenimine), which is one of the most preferred coating material.

To ensure that the shear stress caused by the blood flow is lower than the typical adhesion force between the capture agent (<CFV) and the CTCs/pathogens (which is typically 110±41 nN), the flow length of the hollow fibers 128 of the device 100 preferably varies between 0.5 cm to 50 cm so that the linear flow velocity of the blood within the hollow fibers 128 is maintained in the range $1.8\times10^5$ m/s to $7\times10^5$ m/s along a substantial length of the fibers 128 to ensure a highly efficient capture of the target cells (CTCs or other pathogenic cells) from the blood stream.

To be able to apply typical treatment conditions of 200-500 mL/min blood flow rate resulting in a 4-hour treatment with blood recirculation through the device at 10-20 times, the overall surface of the hollow fibers 128 should be sized to be similar to that of the commercially available hemodialyzer cartridges. In a preferred embodiment, the length of the cartridge body 112 is preferably 1.6 cm but can be varied from 0.5 cm to 50 cm. Again, considering the non-Newtonian flow characteristic of blood, the fluid distributors 124, 125 are arranged in the arterial and venous head spaces 122, 123, respectively.

Figure 3:
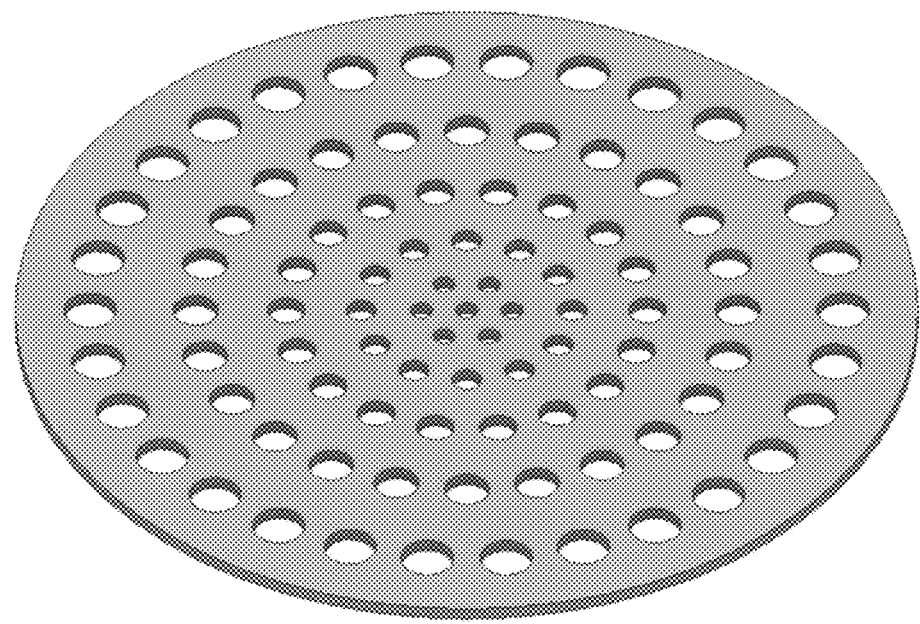
FIG. 3 is a perspective view of a fluid distributor for use in the device shown in FIG. 2.

FIG. 3 shows a specific design of a fluid distributor 300 that can be used in the device 128 shown in FIG. 2. The fluid distributor 300 provides uniform flow distribution over the entire cross sectional area of the cartridge perpendicular to the flow direction of the blood stream within the cartridge. In this embodiment, the fluid distributor 300 contains a central hole and a plurality of holes around it with increasing diameters toward the periphery of the fluid distributor 300. In a specific design of the fluid distributor 300, the diameter of the first pitch circle, which extends around a central hole with a diameter of 3 mm, is 6 mm and contains 6 pieces of holes with 3 mm interior diameter. From the first pitch circle, the interior diameter of the holes are increased by 1 mm, the diameter of the pitch circles are increased by 2 mm and the number of holes are increased by 6 pieces for 4 times.

Within the cartridge body 112, the dialysate flows in countercurrent with the blood, preferably at the same velocity as the blood. By the design of this novel approach, the device 100 provides a dual function of 1) removing target CTCs and/or pathogens; and 2) performing dialysis, which is particularly beneficial when tumor cells or other pathogens are also present in the blood of a patient subject to hemodialysis. It is noted that a cancer commonly causes associated diseases, so in addition to CTC-removal, the blood treatment carried out by means of the device of the present invention is also beneficial to removing toxins from the blood of the treated patient.

Capture Agents

The cartridge of the invention utilizes immuno-affinity capture for cell and/or pathogen removal. Capture agents include but not limited to humanized anti-EpCAM, tumor specific humanized antibodies, folic acid, aptamers, mucin, lectins and any combinations of them. Anti-EpCAM is an antibody against Epithelial Cell Adhesion Molecule (Ep-CAM), that is exclusively expressed by most epithelia originated cancer cells, thus serve as a general target for unique identification and immobilization. Other specific antibodies to certain antigens can also be used either solely or mixed with anti-EpCAM or other binding ligands. In one example, a patient with known colon cancer can be treated with a cartridge having CD44 and EpCAM antibodies. CD44 is specific for cancer cells escaped from colon tumors, while EpCAM is utilized as a general binding agent. Application of a specific antibody reduces any potential for non-specific binding and improves flow-capture efficiency, while EpCAM ensures removal of any additional CTCs.

Folate receptors are highly overexpressed on the surface of many different tumor types including epithelial, ovarian, cervical, breast, lung, kidney, colorectal, and brain cancers. Sarcomas, lymphomas, and cancers of the pancreas, testicles, bladder, prostate, and liver on the other hand usually do not have elevated levels of folate receptors. Therefore, immobilized folic acid can specifically distinguish and bind CTCs, thus serves as potential orthogonal (i.e. orthogonal to antibodies) immobilized capture agent.

Another class of potential capture agents is aptamers, which are oligonucleotides (single-stranded DNA or RNA molecules with stable three-dimensional structures) with high affinity and specificity to bind to targets including CTCs. Aptamers can be selected from huge libraries against known molecules or can be synthetized using common nucleic acid chemistry. Aptamers offer personalized flow-capture technologies through customized polymerase chain reaction (PCR) amplification according to the specific targets.

Lectins also represent potential capture agents. Lectins are a group of proteins that bind specifically and reversibly to mono- and oligosaccharide carbohydrate moieties. Since CTCs have carbohydrate expression patterns different that of normal cells, lectin specific affinities towards certain CTCs can be utilized for efficient cell flow-capture either solely or combined with other agents.

Furthermore, cancer-specific mucin 1 (MUC1) molecule is also upregulated in some cancer diseases. Mucins are strongly glycosylated epithelial originated proteins. Thus, anti-MUC1 can also serve as capture agent.

Since the current application aims the description of the cartridge and its in-situ preparation, the capture agents listed above are only for demonstrative purposes. The current invention describes a cartridge with specially designed flow characteristics to ensure highly efficient irreversible capture of CTCs and/or pathogens due to the utilization of strictly controlled flow patterns with simultaneous hemodialysis.

Immobilization Chemistry

In the prior art [Simard, L., et al., Means for the biological purification of a biological fluid. 2001, U.S. Pat. No. 6,260,715 B1; Pachmann, K. and U. Pachmann, Method for quantitative detection of vital epithelial tumor cells in a body fluid. 2003, US2003017514; Korbling, M., et al., Devices and methods for extracorporeal ablation of circulating cells. 2011, U.S. Pat. No. 8,057,418 B2; Yoshioka, S., Cell treatment device, cell treatment cartridge and body fluid treatment system. 2010, U.S. Pat. No. 9,526,823 B2.] one can find different methods to immobilize antibodies on solid supports. As one example, anti-EpCAM antibody is immobilized on polysulfone hollow fibers during the manufacturing of the cartridge. In the first step the cartridge is exposed 2-3 hours long to a solution of 4% human serum albumin (HSA) in order to ensure proper HSA adsorption on the fiber surface preferably at room temperature. The adsorbed HSA is then cross-linked with 2% glutaraldehyde. Excess glutaraldehyde is rinsed with deionized water. In the next step the cartridge is filled with an appropriate reducing coupling buffer containing 2-3 mg/ml of the anti-EpCAM and reacted for 1-2 hours at room temperature. Then, excess reagents and antibodies are washed off using ethanolamine Finally, the cartridge is rinsed with sterile phosphate-buffered saline buffer and dried with sterile air.

In another example, folic acid is immobilized onto the surface of polysulfone hollow fibers during cartridge manufacturing starting with chloromethylation of the polysulfone membrane by conventional Friedel-Crafts catalysis reaction, e.g., washing with the chlorodimethyl ether, hexane and $SnCl_4$, which is well known procedure for a person skilled in the art. Afterwards, deamination of the chloromethylated polysulfone membranes is performed by ethylenediamine at room temperature. Then the cartridge is leached with 0.1 M 2-(N-morpholino) ethanesulfonic acid and rinsed with deionized water. In the next step the cartridge containing the hollow fibers is filled with 15-30 mg/mL of folic acid solution and N-ethyl-N'-(3-dimethylaminopropyl)carbodiimide hydrochloride (EDC) and reacted for 1-2 hours at room temperature. Alternatively, EDC can be substituted with N,N'-methanetetraylbis [cyclohexanamine] (DCC). The excess reagents are washed off using 10 mM 4-(2-hydroxyethyl)piperazine-1-ethanesulfonic acid buffer (HEPES) and then by deionized water.

In-Situ Preparation of the Multifunctional Cartridge

Another important aspect of the current invention relates to a method of in-situ producing a blood treatment device according to the present invention. Currently available dialyzers apply semi-permeable membranes, which are passive elements of the cartridges, i.e., hemodialysis is governed by chemical potential difference (i.e., osmotic pressure difference) through the membrane. Membrane flux is not selective thus cut-off threshold (i.e., molecular mass) is controlled by pore size difference and pressure difference.

In the device production method of the invention, the blood treatment device is activated in-situ with immunoaffinity technique using one or more binding agents mentioned above.

In the first step 410, a sterile extracorporeal blood treatment device is provided without any binding agent and capture chemistry. This kind of device may be readily available, for example, as a hemodialysis cartridge from equipment manufacturers, such as vendors offering conventional dialyzers.

In a second step 420, a predetermined amount of a specific binding agent or various binding agents are provided in the form of solution(s) at appropriate concentration(s) in package(s), for example in plastic bag(s). The packages and their contents may be previously sterilized by conventional gamma-irradiation.

The packages containing the binding agents are preferably prepared in the same way as the standard medical infusion solutions including degassing and unique identification of the packages, for example by bar codes.

In a third step 430, the adsorptive surface of the filter unit of the blood treatment device is subject to the solution of the binding agent, or subsequently to various solutions at the location of the treatment process. The one or more solutions of the binding agent(s) may be circulated through the hollow fibres of the device in an accurately controlled manner, or alternatively, the device may be immersed into the solution of the binding agents under sterile conditions. In the former case, the solution of the binding agent(s) is preferably circulated through the hollow fibers of the dives using a pump system.

As a result of the above step of applying the binding agent on the adsorptive surface of the filter unit, the device is brought into an activated state and thus ready for use in a blood treatment process.

The above activation procedure has the advantage that both the blood treatment device and the binding agent solution can be kept under sterile conditions till the actual use thereof, and activation of the device can be carried out at the location of the blood treatment (i.e. where the patient stays) right before starting the treatment.

When the blood treatment device is used in hemodialysis, the sterile device (e.g. cartridge) may be installed in a hemodialyzer machine for its activation. A commercially available dialysis machine may be suitable for this purpose, but its control software should be modified to be capable of performing the activation process. In an additional step, the solution's package may be connected to the dialyzer machine to allow the solution to flow out from the package into the dialysis machine and thus the passive device is getting activated by exposing its filter unit to the binding agent contained in the solution. Exposing conditions (e.g. time, flow rate, temperature, etc.) are controlled by the dialysis machine according to the special demands of the particular treatment.

In a preferred embodiment of the method, when more than one binding agents are used in separate packages, the various solutions are switched automatically by the machine using multi-ways valves. Alternatively, the different solutions may also be switched manually by the operator. Both in automatic and manual switching modes, the packages are barcode-labeled in order to ensure unique identification of the packages.

Figure 4:
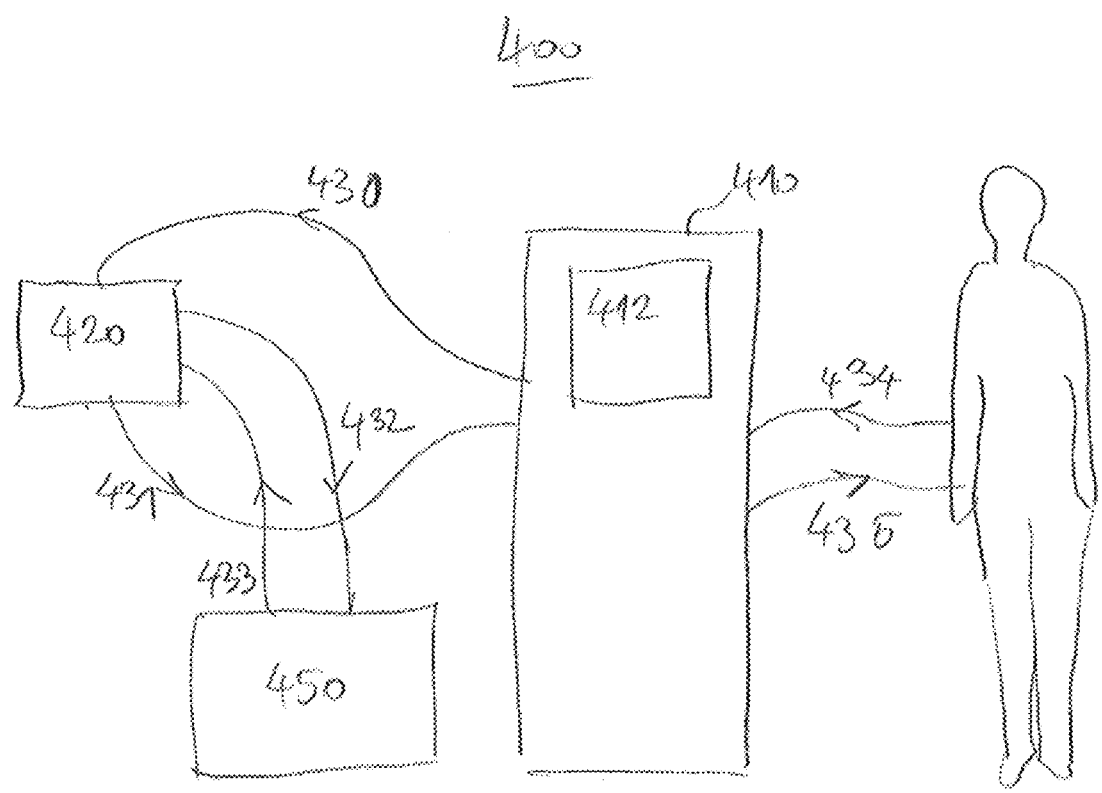
FIG. 4 is a schematic block diagram of a blood treatment system according to the present invention.
Figure 6:
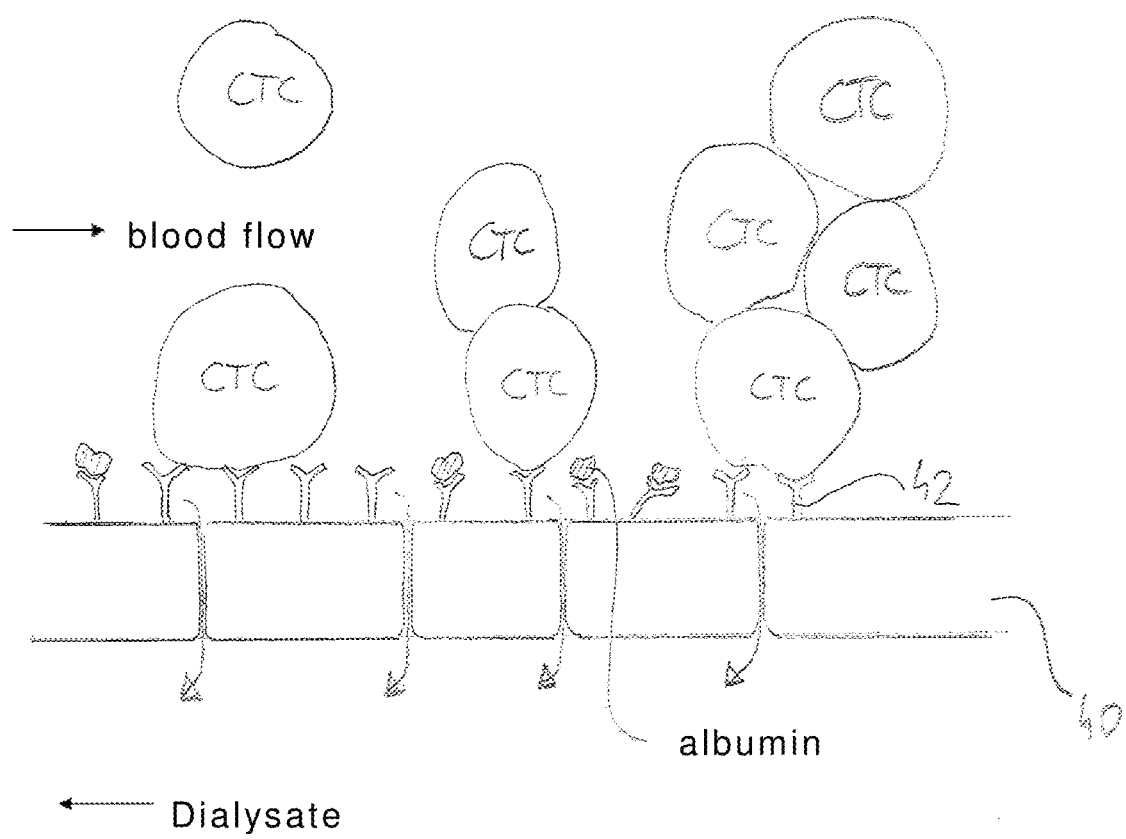
FIG. 6 illustrates a process which takes place under the operation of the invention. Binding agents having specific binding sites to bind cancer cell have capturing cells attached to them. Such capturing cells in this embodiment are the same as CTCs. The non-specific binding sites are covered by serum albumin. CTCs in the blood stream are bound by the capturing cells which are here identical with the CTCs and clusters are formed. Thereby the blood is depleted in CTCs. The process is assisted by convection flow through the pores of the membrane preferably a high flux membrane in this embodiment.

In a further aspect of the present invention, a system is provided for operating the blood treatment device according to the present invention. The functional block diagram of this system is illustrated in FIG. 4. The system 400 comprises a dialysis machine 410, which is attached to a blood treatment device 420 according to the invention via respective pipes 430, 431, 432, 433 for circulating the blood of a patient and a dialysate through the blood treatment device 420. The system further comprises a dialysate container 450 for storing a dialysate to be used in a blood treatment. The dialysis machine 410 is equipped with respective pipes 434, 435 for receiving and returning a patient's blood.

The dialysis machine 410 includes a control unit 412 for controlling the operation of the machine. Beyond the common and well-known operational functions of this kind of machine, the control unit 412 further functions to control the flow velocity within the hollow fibers of the device at a predetermined value, for example at a flow velocity within the range of $1.8 \times 10^{-5}$ m/s to $7 \times 10^{-5}$ m/s. As mentioned above, in case of the formation of a cluster at any location within a hollow fiber of the blood treatment device, the actual flow velocity may increase, possibly resulting in destruction of the cancer cells forming the clusters, which might be bound to the membrane surfaces of the hollow fibers of the blood treatment device.

In this patent application, immobilization experiments with two kinds of binding agents and on two different kinds of membranes are summarized as examples.

The experimental conditions were tested in single cycle (chemicals were contacted with membrane's surface one time only) and continuous modes (chemicals were circulated repeated times).

The single cycle or batch mode is also appropriate to prepare a device according to a preferred embodiment, wherein the CTCs of the patient are bound to the membrane and non-specific binding sites are covered by protein molecules, in particular serum albumin of the patient. This embodiment has the advantage that the serum albumin of the patient is necessarily non-immunogenic to the patient. Moreover, tumor cells, e.g. CTCs from own blood of the patient have probably the highest affinity against further CTC we wish to capture. In fact, in this case CTCs act like capture agents and the binding agent like antibodies.

In this embodiment CTCs are bound to the binding agent added to the membrane, preferably the semi-permeable membrane and serve as capture agents Results of various analytical measurements and actual CTC capture experiments are reported to proof the performance of the systems.

Example 1

Polysulfone/Anti-EpCAM System (Single Cycle)

Figure 7:
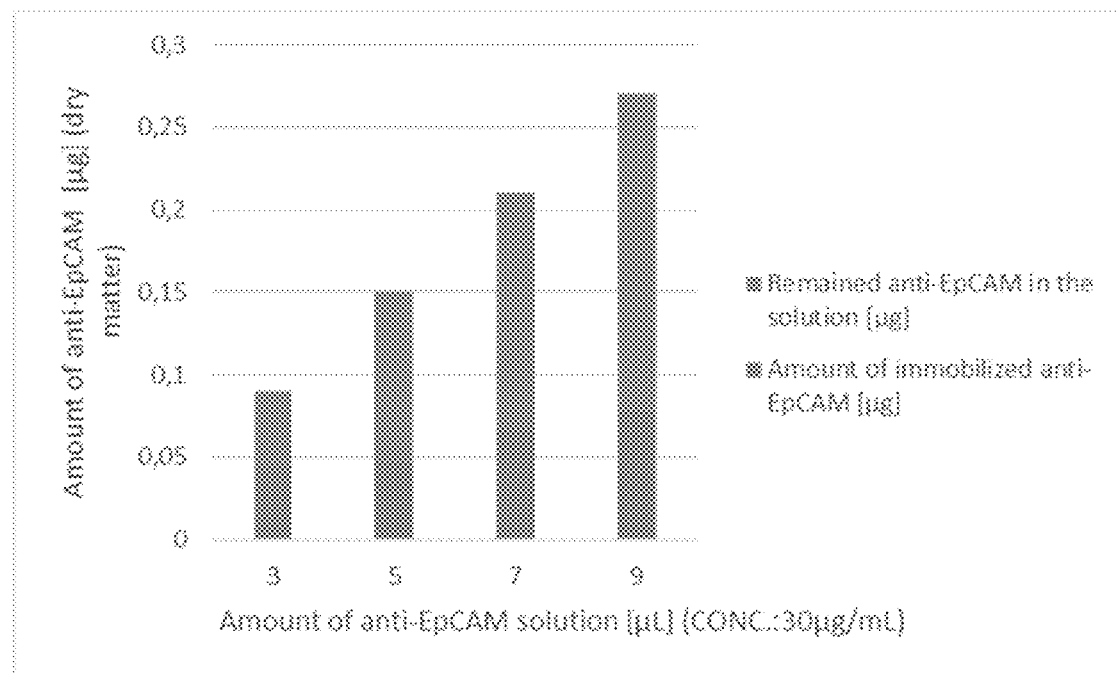
FIG. 7 shows the Anti-EpCAM immobilization onto polysulfone membrane

The aim of the present example was the determination of the maximum anti-EpCAM amount, which can be immobilized onto the surface of a single membrane hollow fiber. Stock solution of 30 µg/mL anti-EpCAM mixture was used. The investigated range of the amount was 3-9 µL anti-EpCAM/100 µL buffer. Based on FIG. 7 one can conclude that 9 µL stock solution have to be used to reach the saturation of the surface with EpCAM. Furthermore, FIG. 7 shows that the utilized anti-EpCAM mixture can be further used in recirculation experiments.

Figure 8:
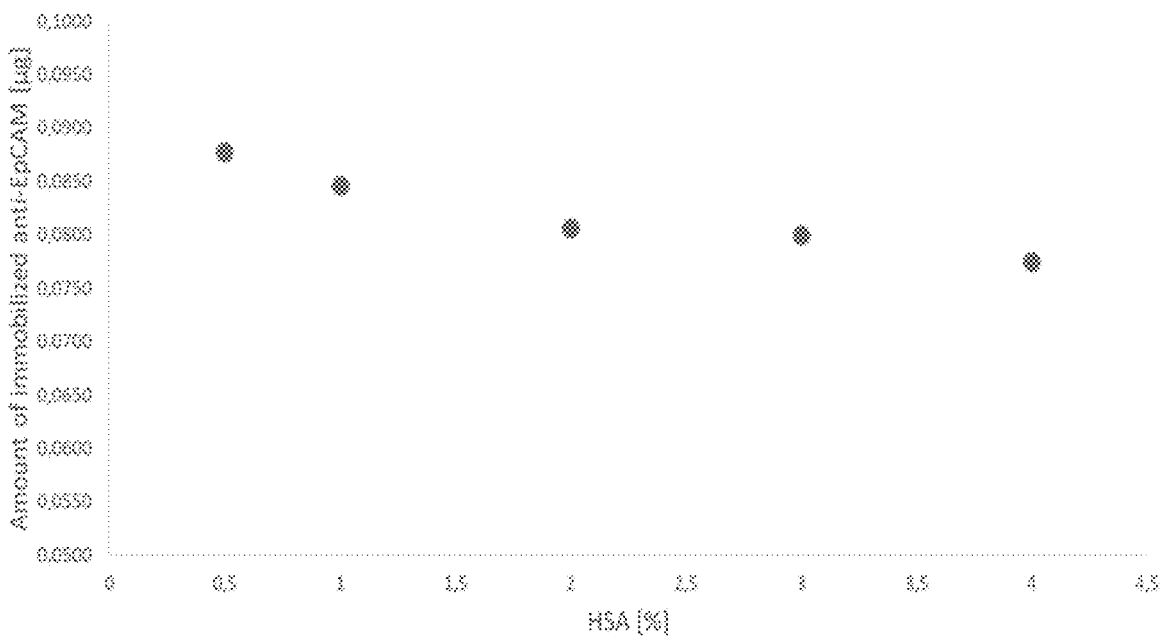
FIG. 8 illustrates the setting the required HSA concentration for anti-EpCAM immobilization

We also aimed at determination of the appropriate HSA concentration, which required for the anti-EpCAM immobilization. The investigated HSA concentration range was varied between 0.5-4 V/V %. For the HSA optimization measurements 0.3 µg of anti-EpCAM was used in each experiments. FIG. 8 shows the amount of immobilized anti-EpCAM onto the polysulfone membrane. Thorough analysis of FIG. 8 suggest that the optimal concentration of HSA was 2 V/V %, which covers the majority of all non-specific binding sites.

We also aimed at determination of the appropriate glutaraldehyde concentration, which is a required crosslinking reagent for the anti-EpCAM immobilization. Glutaraldehyde is required for the proper formation of peptide binding. The investigated glutaraldehyde concentration was varied between 1-5 w/w %. For the glutaraldehyde concentration setting measurements 0.27 µg of anti-EpCAM was used in each experiments. The preferred concentration of glutaraldehyde was found to be 2-3 w/w %.

Optimal concentrations of the reagents required for the anti-EpCAM immobilization in a single cycle experimental setup can be readily applied in the continuous flow measurements but their further optimization is necessary.

Example 2

Polysulfone/Anti-EpCAM System (Continuous Flow Experiments)

All continuous flow experiments were carried out using an in-house developed small batch system. The system contains 15 polysulfone (PSF) hollow fibers, which were fixed into an approximately 15 cm long polyurethane tube by FBS acetic acid based glue. The solutions were loaded into the membranes by peristaltic pump. The optimized process of immobilization is as follows:

Human serum albumin (HSA) immobilization onto PSF internal surface to prevent non-specific binding of blood proteins on the membrane surface. It was found that the flow rate can be varied in the range of 0.5-10 ml/hour, while the duration was 0.5-2 hour. The preferred condition is 1 hour treatment with 2 ml/hour flow rate.

Glutaraldehyde crosslinker: glutaraldehyde was loaded into the system as a crosslinker between HSA and anti-EpCAM. The concentration can be ranged from 1% to 10%, while in the preferred embodiment it is around 2-3%.

Glutaraldehyde solution's flow rate was varied in the range of 0.5-10 ml/hour for 30-120 minutes duration.

HPLC grade water: The excess of glutaraldehyde was remove by rinsing the hollow fibers using HPLC grade water.

HPLC grade water was loaded at 0.5-10 ml/hour (preferred 6 ml/h) flow rate for 0.5-2 hour, while the preferred is 0.5 hour.

Immobilization of anti-EpCAM

Based on the preliminary results (see Example 1 above) the concentration of anti-EpCAM could be 0.1-50 µg/ml, but the preferred concentration is 5 µg/ml. The flow rate of the anti-EpCAM solution can be varied in the range of 0.5-10 ml/hour for 0.5-6 hour duration. The preferred parameters are 6 ml/hour for 20 min.

Picoline borane can be used as reducing agent for the Schiff base based immobilization. The essential point of this experiments is the finding of proper solvent for picoline borane which does not precipitate the solute or influence the biological functions of the antibody. Firstly, solvents were tested on magnetic beads functionalized by amine groups.

Solvents for picoline borane:
  Picoline borane in 20-80 v/v % DMSO. The optimal concentration is 50 v/v % DMSO (0.1-2 mg/ml concentration, but preferred 1 mg/ml).
  Picoline borane in 20-80 v/v % DMF. The optimal concentration is 50 v/v % DMF (0.1-2 mg/ml concentration, but preferred 1 mg/ml).
  Picoline borane in 1-30 v/v % EtOH 1 mg/ml. The optimal concentration is 5 v/v % EtOH.

HPLC grade water

HPLC grade water was loaded at 0.5-10 ml/(preferred 6 ml/hour) for 0.5-2 hour, preferred 0.5 hour into the hollow fibers.

Ethanolamine washing is necessary to set the pH for the following steps

Ethanolamine solution (50-250 mM, preferred 150 mM) was loaded in to the system at 0.5-10 ml/hour for duration of 0.5-2 hour, preferred 6 ml/hour for 60 min.

CTCs in PBS solution were captured at 0.5-10 ml/hour by the immobilized anti-EpCAM. The optimal flow rate was 6 ml/hour.

Example 3

In a proof of concept experiment indicating that anti-EpCAM can capture CTCs magnetic beads were used to immobilize anti-EpCAM. The beads were used to prove that anti-EpCAM antibody binds the CTCs (modeled by Colon carcinoma cells HT29) under flow conditions. It is shown that CTCs form clusters, i.e. the CTC bound binds further CTCs with a high specificity. It has also been found that immobilized anti-EpCAM binds CTC (colon HT29 cells) an polysulfone membrane of a hollow fiber.

Example 4

The aim of this experiment was the investigation of the 1 mg/ml picoline borane in 5% EtOH buffer for anti-EpCAM immobilization in the continuous system. FIG. 11 shows the intensity (directly proportional to the concentration) of the non-immobilized anti-EpCAM. Samples were collected in every 30 minutes. The initial point means the intensity of the initial anti-EpCAM solution. Buffer: 1 mg/ml picoline borane in HPLC grade water (95%) and EtOH (5%) solution. The anti-EpCAM solution concentration was 5 µg/ml. FIG. 11 also shows that the initial concentration of anti-EpCAM significantly decreased, which verifies that picoline borane is an alternative coupling buffer Major Points of the Optimization Process of Anti EpCAM Immobilization:

Various flow rates and durations for HSA adsorption onto the membrane's surface were investigated. Table 1 shows the measured HSA concentrations by UV spectroscopy in the function of the applied flow rates. Based on the results that the optimal flow rate is 2 ml/hour.

TABLE

1. Experimental results of HSA flow rate optimization

| Time [min] | Intensity [ops] | Wavelength [nm] |
|---|---|---|
| HSA: 6000 µL/h | | |
| 30 | 13 044 | 333.55 |
| 60 | 13 023 | 334.45 |
| 90 | 12 679 | 336.28 |
| 120 | 13 050 | 335.49 |
| HSA: 4000 µL/h | | |
| 30 | 14 139 | 336.55 |
| 60 | 12 585 | 336.28 |
| 90 | 12 932 | 338.31 |
| 120 | 11 911 | 335.73 |
| HSA: 2000 µL/h | | |
| 30 | 12 444 | 335.2 |
| 60 | 12 440 | 334.45 |
| 90 | 12 410 | 338.68 |
| 120 | 11 966 | 335.55 |

It was observed that how much time is needed to the immobilization in the case of 2000 µl/hour. In Table 2 the results of the measurements show that 60 min is necessary for the immobilization of anti-EpCAM at 2000 µl/hour flow rate.

TABLE

2. Experimental results of HSA contact time optimization

| Test point | HSA: 30 min, 2000 µl/h | | HSA: 60 min, 2000 µl/h | |
|---|---|---|---|---|
| | Intensity [ops] | Wavelength [nm] | Intensity [ops] | Wavelength [nm] |
| In | 53 288 | 515.69 | 50 677 | 516.12 |
| Out | 31 194 | 516.06 | 35 348 | 516.22 |
| Re1 | 34 916 | 515.74 | 21 730 | 515.06 |
| Re2 | 30 536 | 516.26 | 19 937 | 515.06 |

In order to reduce the immobilization process time, the flow rate of the HSA solution was doubled and the time was halved. The intensity of anti-EpCAM solutions were measured by fluorimeter. The samples was diluted to 10 times before fluorimetric measurements (Extinction: 488 nm, Scan range: 500-550 nm, Emission: 514). Table 3 shows the results. The outcome of the investigation was that much less anti-EpCAM immobilized to the surface in the case of less time and faster flow rate.

TABLE

3. Experimental results of HSA contact time optimization II.

| Test point | HSA: 60 min, 2000 µl/h | | HSA: 30 min, 4000 µl/h | |
|---|---|---|---|---|
| | Intensity [ops] | Wavelenght [nm] | Intensity [ops] | Wavelength [nm] |
| In | 24 880 | 514.12 | 32 187 | 514.96 |
| Out | 24 005 | 518.06 | 25 769 | 515.01 |
| Re1 | 26 521 | 514.96 | 24 875 | 515.22 |
| Re2 | 17 957 | 515.96 | 21 045 | 516.01 |

Example 5

In this example workflow of cell capturing experiments is described: 1.) Subculturing of cell lines 2.) Determination of initial cell concentration 3.) CTC capturing by the invented device 4.) Determination of final cell concentration 5.) Statistical evaluation of the capturing efficiency.

Example 5.1

Sub Culturing of Cell Lines (HT29 Colon and M1/9 Melanoma)

The cells were stored in an incubator (Cellstar, Mount Holly, N.J.) at 37° C. with 5 V/V % $CO_2$ (Messer Hungarogaz Kft, Budapest, Hungary) environment. The cells were checked before each experiments by microscopic observation. The viable cells were adhered to the bottom of the cell culture flask (TPP, Trasadingen, Switzerland). Sterile work conditions were maintained during the conventional cell culturing. The adherent cells were sorted from non-viable cells and remained nutrients and metabolites by 1×PBS buffer solution. Purified cells were picked up by chelating agents (EDTA) and/or enzymes (trypsin). Melanoma cells were picked up by EDTA at concentration 0.02 w/w %. Colon cancer cells were picked up by Trypsin-EDTA purchased from Sigma (T4174, St. Louis, Mo.), which was diluted to 10 times. 0.5 ml of EDTA or trypsin-EDTA solution was added to the purified cells and they were stored in the incubator for 5 minutes. Subsequently, the flask was mixed by vortexing to support releasing step. EDTA or trypsin-EDTA solution in the cell culture flask was diluted by 1 ml PBS buffer. The cell culture flasks were put back into the incubator again for 5 minutes. They were also vortexed. The extent of released cells were monitored by microscope. If most of the cells were in solution, the suspension was pippeted into a sterile eppendorf tube (2 ml) in order to centrifuge the mixture. The supernatant was removed. The pellet was picked up in PBS or blood (300 µl), which depends on the aim of the experiment.

Example 5.2

Determination of the initial cell concentration in PBS was defined with Bürker chambers. Milled grooves of Bürker chamber divide the surface into two large well-defined fields. One field is divided into 144 squares. One square's sides are 0.2 mm Cells were counted on 24 pieces of these squares in diagonal direction plus 1 random square. When a cover glass was placed on top, there was a gap of 0.1 mm between the glass and the field. The volume of the counted cell suspension is 1 ml (0.2 mm×0.2 mm×0.1 mm×25×10 000). The whole Bürker chamber (including the cover glass) was assembled preliminary 10 µl of cell suspension was injected under the fixed cover glass. Cell number was visually counted under a microscope. The cells were counted on 1 $mm^2$ area. The cell concentration is counted cell number multiplied by 10 000 and the resulted number shows the number of cells in 1 ml suspension. Counting of CTCs in blood was different due to its high density. Firstly, the red blood cells were eliminated by BD FACS lysis buffer (Backton-Dickinson, Franklin Lakes, N.J.). The blood samples were diluted to 5 times with BD FACS. The counting method was the same as in PBS. Each experiment samples were counted three times both the inlet and outlet. The final result of these parallel countings was the statistical average of the three values.

Cell suspension in PBS or blood was introduced into the developed model system (binding agents were immobilized on hollow fibres). Flow rate of 6 ml/hour was assured by high precision ultra-low flow peristaltic pump VWR (Radnor, Pa.).

At the end of the experiments, the final concentration of suspension was also determined by Bürker chamber cell counting. The efficiency of capturing was evaluated with the comparison of initial and final concentrations in percentage.

Example 6

Cell Capturing Experiments Utilizing Anti-EpCAM/Polysulfone/PBS Model System

CTC capturing efficiency was investigated in the function of different anti-EpCAM concentrations. All chemicals were from Sigma-Aldrich (St Louis, Mo.). Hollow fibers were pretreated with HSA using 2 ml/hour flow rate for 1 hour duration. Subsequently, glutaraldehyde was loaded into the hollow fibers at 0.5 ml/hour flow rate for 1 hour duration. Excess of applied reagents were washed out with HPLC grade water at 1 ml/h for 0.5 hour. Flow rates were controlled with syringe pump (New Era Pump System, Fermingdale, N.Y.). Two different anti-EpCAM solutions were investigated: 2.7 µg/ml and 5 µg/ml. Commercially available anti-EpCAM solution (LifeTechnologies, Fredrick, Md.) was added to the 1 mg/ml picoline borane in 5 V/V % EtOH coupling buffer. Anti-EpCAM in the coupling buffer was flowed through the system at 6 ml/hour for 20 minutes. The anti-EpCAM solution was recirculated two times. Excess of applied reagents were washed out with HPLC grade water at 1 ml/h for 0.5 hour. In order to maintain the pH ethanolamine solution (150 mM) was loaded in to the system at 1 ml/hour for duration of 0.5 hour. Using same parameters PBS was also used as a washing buffer. To evaluate the immobilization process cell suspension (HT29 colon cells) in PBS was loaded into the in house developed pilot system. Flow rate was controlled by high precision ultra-low flow peristaltic pump (Ismatech, Wertheim, Germany) at 6 ml/hour. Initial cell concentration of introduced suspension in PBS is measured with Bürker chambers. Furthermore, at the end of the experiment the final concentration of suspension was also measured by Bürker chamber based cell counting. The efficiency of different anti-EpCAM concentrations were evaluated with the comparison of initial and final concentrations of cells in percentage. Efficiency at 2.7 µg/ml and 5 µg/ml anti-EpCAM concentrations were 76.45% and 82.5%, respectively.

Example 7

Cell Capturing Experiments Utilizing Anti-EpCAM/Polysulfone/Mice Blood Model System CTC capturing efficiency was investigated at different anti-EpCAM concentrations. Hollow fibers were pretreated with HSA at 2 ml/hour flow rate for 1 hour duration. Subsequently, glutaraldehyde was loaded into the hollow fibers at 0.5 ml/hour flow rate for 1 hour duration. Excess of applied reagents were rinsed with HPLC grade water at 1 ml/h flow rate for 0.5 hour duration. Flow rates were controlled by syringe pump (New Era Pump System, Fermingdale, N.Y.). Two different anti-EpCAM solutions were investigated: 5 µg/ml and 7.5 µg/ml. Commercially available anti-EpCAM solution (LifeTechnologies, Fredrick, Md.) was added to the 1 mg/ml picoline borane in 5 V/V % EtOH coupling buffer. Anti-EpCAM in the coupling buffer was flowed through the system at 6 ml/hour flow rate for 20 minutes duration. The anti-EpCAM solution was recirculated two times (three times all together). Excess of applied reagents were washed out with HPLC grade water at 1 ml/h flow rate for 0.5 hour duration. In order to set the pH ethanolamine solution (150 mM) was loaded in to the system at 1 ml/hour for duration of 0.5 hour. At the same parameters PBS was also used as a washing buffer. The anti-EpCAM immobilization on polysulfone was evaluated by loading CTCs (HT29) in blood into the above mentioned model system. Flow rate was controlled by high precision ultra-low flow peristaltic pump (Ismatech, Wertheim, Germany) at 6 ml/hour flow rate. Initial cell concentration of the loaded blood stream is measured using Bürker chamber based cell counting method. Before counting CTCs in blood,—due to its high density—the red blood cells has to be destroyed by cell lysis buffer (BD FACS). The blood samples were diluted to 5 times with BD FACS. Final concentration of CTCs in blood was also measured by Bürker chamber based cell counting. The efficiency of different anti-EpCAM concentrations were evaluated with the comparison of initial and final concentrations of cells in percentage. Efficiency at 5 µg/ml and 7.5 µg/ml anti-EpCAM concentrations were 62% and 68%, respectively.

Example 8

Polysulfone/Folic Acid (Single Cycle System)

Folic acid was immobilized on polysulfone membrane. FIG. 12 shows the proof of concept style experiments. Folic acid was immobilized on aminated magnetic beads according to the polysulfone immobilization recipe to prove folic acid bound CTCs modeled by colon carcinoma HT29 cells. On FIG. 12.2 it is shown that folic acid was immobilized on polysulfone surface, CTC was bound by folic acid and the CTCs (colon HT29) were captured.

Please note, in this single cycle experimental setup a harmful and reactive reagent (chlorodimethyl ether) was used, which ruined the external and internal parts of the continuous system.

Example 9

Nephral ST/Anti-EpCAM (Continuous System)

Example 9.1— Preparation of Nephral ST/Anti-EpCAM System

Nephral ST is a hollow fiber material. Previously developed immobilization protocols can be used after minor modifications. Ultra-low flow rate peristaltic pumps were applied. In each cases the employed flow rate was 6000 µl/hour.

Human serum albumin (HSA): The parameters of HSA adsorption could be 0.5-10 ml/hour (preferred 6 ml/hour) for 0.1-2 hour, preferred 20 min. The concentration of HSA solution could be 10-50 mg/ml, preferred 40 mg/ml which were loaded into the hollow fibres.

Glutaraldehyde crosslinker: The parameters of glutaraldehyde could be 0.5-10 ml/hour (preferred 6 ml/hour) for 0.1-2 hour, preferred 20 min. The concentration of glutaraldehyde could be 1-10 V/V %, preferred 2 V/V %

HPLC grade water the excess of glutaraldehyde was remove by HPLC grade water.

HPLC grade water was loaded at 0.5-10 ml/hour (preferred 6 ml/hour) for 0.5-2 hour, preferred 0.5 hour into the hollow fibres.

Immobilization of anti-EpCAM

The concentration of anti-EpCAM was 5 µg/mL in picoline borane coupling buffer (5 V/V % EtOH). It is important to mention that the picoline borane solution has to be made freshly at least weekly. The applied flow rate could be 0.5-10 ml/hour for 0.1-6 hour. The preferred parameters are 6 ml/hour for 20 min in each recirculation step.

Potential alters of coupling buffers:

Cyanoborohydride coupling buffer

Picoline borane in 20-80 V/V % DMSO. The optimal concentration is 50 v/v % DMSO (0.1-2 mg/ml concentration, but preferred 1 mg/ml).

Picoline borane in 20-80 V/V % DMF (Dimethylformamide). The optimal concentration is 50 V/V % DMF (0.1-2 mg/ml concentration, but preferred 1 mg/ml).

Picoline borane in 1-30 v/v % EtOH 1 mg/ml. The optimal concentration is 5 V/V % EtOH.

HPLC grade water the excess of chemicals were remove by HPLC grade water. HPLC grade water was loaded at 0.5-10 ml/hour (preferred 6 ml/hour) for 0.5-2 hour (preferred 0.5 hour) into the hollow fibres.

Ethanolamine washing 50-250 mM (preferred 150 mM) ethanolamine was rinsed at 0.5-10 ml/hour (preferred 6 ml/hour) for 0.5-2 hour, preferred 0.5 hour into the hollow fibres to set and maintain the appropriate pH.

PBS PBS was flowed at 0.5-10 ml/hour (preferred 6 ml/hour) for 0.5-2 hour, preferred 0.5 hour into the hollow fibers.

CTCs in PBS solution were captured also at 0.5-10 ml/hour, preferred 6000 µl/hour.

Example 9.2—Capturing CTCs from PBS with Nephral ST/Anti-EpCAM System

With the help of this procedure (based on above mentioned methods) 50-80% of circulating tumor cells could be captured from PBS.

Example 10—Nephral ST/Folic Acid (Continues System)

Example 10.1—Preparation of Nephral ST/Folic Acid System

Immobilization of folic acid has a simple process on the Nephral ST. The amine groups of the membrane can covalently bind the folic acid through crosslinkers (NHS, EDC, DCC). The solvent of folic acid is a crucial question. Folic acid is minimally soluble in water. It is important to mention that dimethyl sulfoxide (DMSO) is an excellent organic solvent in addition it is a good opportunity for using DCC instead of EDC.

The molar ratio is essential connecting to successful of capturing. Different molar ratios are available in the literature see Table 4.

TABLE 4. Various molar ratios of reagents for folic acid immobilization

| Molar ratio | Folic acid [mol] | DDC [mol] | NHS[mol] |
|---|---|---|---|
| A | 1 | 1.1 | 2.2 |
| B | 1 | 2.2 | 4.4 |
| C | 1 | 2 | 2 |

Our preliminary results show that case "A" serves the best cell capture efficiency, which was determined based on cell counting (Bürker chambers).

EDC has certain advantageous properties such as it reacts with carboxylic acid moieties to form an active O-acylisourea intermediate that is easily displaced by nucleophilic attack from primary amino groups in the reaction mixture. The primary amine forms an amide bond with the original carboxyl group, and an EDC by-product is released as a soluble urea derivative. The O-acylisourea intermediate is unstable in aqueous solutions; failure to react with an amine results in hydrolysis of the intermediate, regeneration of the carboxyls, and the release of an N-unsubstituted urea.

MES buffer (4-morpholinoethanesulfonic acid) is a suitable carbodiimide reaction buffer. Phosphate buffers and neutral pH (up to 7.2) conditions are compatible with the reaction chemistry, albeit with lower efficiency; increasing the amount of EDC in a reaction solution can compensate for the reduced efficiency.

N-hydroxysuccinimide (NHS) or its water-soluble analog (Sulfo-NHS) is often included in EDC coupling protocols to improve efficiency or create dry-stable (amine-reactive) intermediates. EDC couples NHS to carboxyls, forming an NHS ester that is considerably more stable than the O-acylisourea intermediate while allowing for efficient conjugation to primary amines at physiologic pH.

DCC (dicyclohexyl carbodiimide) crosslinks carboxylic acids to primary amines in the same manner as EDC (see reaction schemes above). However, because DCC is not aqueous-soluble, it is primarily used in manufacturing and organic synthesis applications rather than in the typical protein research biology lab.

The preferred immobilization procedure is based on the following steps: Load into the membrane hollow fibres a mixture of folic acid (concentration: 0.01-0.5 mg/ml) in 50% DMSO and 50% MES buffer (0.1 M) and crosslinkers (NHS and EDC). A neutralization process was carried out by 10 mM HEPES buffer and HPLC grade water. The last step is the CTC capturing from PBS or blood.

Major Points of the Optimization Process of Folic Acid Immobilization:

Decision was made about the suitable molar ratio based on the numbers of captures CTCs in the case of "A" molar ratio (1 folic acid: 2.2 DDC: 4.4 NHS) we could captured 70% while in the case of "B" we captured 61.5%.

We investigated which crosslinkers should be used for instance DDC or EDC. As it is mentioned before DDC causes an intermediate product, which is avoidable with the use of EDC in water medium. Beside EDC could be used MES buffer instead of harmful organic solvents. In spite of this advantages of EDC, it may not be as efficient as DDC.

Example 10.2—Capturing CTCs from PBS with Nephral ST/Folic Acid System

With the help of this procedure (based on above mentioned methods) 50-70% of circulating tumor cells could be captured from PBS.

HSA could be replaced by the human blood to prevent allergic reaction or non-biocompatibility.

Example 11—Summary of Capture Experiments

The recirculation of the reagents could help the immobilization process. Recirculation of blood including CTCs can increase the efficiency of the capturing.

TABLE 5. Summary of the capture efficiency in the case of different membranes and binding agents

| Captured CTCs [%] | Anti-EpCAM | Folic acid |
|---|---|---|
| Polysulfone | 80-85 | N/A |
| Nephral ST | 70-86 | 47-70 |

Industrial Application and Intended Use

Intended use of the current invention includes CTC and/or pathogen removal treatment during operation, post-operation and as preventive treatment. During operation mode entails removal of CTCs during surgical operation and/or biopsy since both can cause the uncontrolled release of tumor cells into the blood stream. Pathogen removal utilizing the additional hemodialysis mode reduces the risk of tumor metastasis caused by escaped cells and helps to maintain the normal blood/serum homeostasis by dialysis of uncontrolled level of metabolites generated by the tumor cells. Furthermore, dialysis during surgery allows the use of drugs, which cannot be otherwise applied due to long residence time addressing safety issues [Copeland, R. A., The drug-target residence time model: a 10-year retrospective. Nat Rev Drug Discov, 2016. 15(2): p. 87-95.]. Post operation mode removes potential CTCs from the circulation after tumor surgery, or cells shed newly into the blood from intact or unknown (invisible for medical imaging) tumor. Post operation mode also plays an important role in cancer treatment when the primary tumor or any metastasis is not operable. Furthermore, the use of the invented device and method reduces the required number of chemo- and radio-therapies as a part of conventional cancer treatments. Another important mode is the prevention. Once a person is predisposed to cancer based on any kind of genomic testing, preventive pathogen removal treatment may help to avoid tumor or metastasis formation.

REFERENCES

Alberts B, Johnson A, Lewis J, et al. Molecular Biology of the Cell. 4th edition. New York: Garland Science; 2002.

Isolating Cells and Growing Them in Culture. Available from: https://www.ncbi.nlm.nih.gov/books/NBK26851/].

Autebert, J., et al., Microfluidic: an innovative tool for efficient cell sorting. Methods, 2012. 57(3): p. 297-307.

Copeland, R. A., The drug-target residence time model: a 10-year retrospective. Nat Rev Drug Discov, 2016. 15(2): p. 87-95.

Gaitas, Angelo and Kim, Gwangseong, Chemically Modified Plastic Tube for High Volume Removal and Collection of Circulating Tumor Cells. PLoS ONE 10(7): e0133194.

Gaitas, Angelo and Kim, Gwangseong, US2015121808A1

Kim, M. Y., et al., Tumor self-seeding by circulating cancer cells. Cell, 2009. 139(7): p. 1315-26.

Korbling, M., et al., Devices and methods for extracorporeal ablation of circulating cells. 2011, U.S. Pat. No. 8,057,418 B2.

Kufe, Donald W et al. (Eds) Holland-Frei Cancer Medicine, 6th edition Hamilton (ON): BC Decker; 2003. ISBN-10: 1-55009-213-8].

Lacy-Colson, Jon, Apheresis device and related methods 2011 GB2479536A

McNeil, Gary L, 2014 blood is separated with various filters. US2014074007A1

Meng, J., et al., Adhesion between peptides/antibodies and breast cancer cells. Journal of Applied Physics, 2010. 107(11): p. 114301.

Mitra A. et al. Technologies for deriving primary tumor cells for use in personalized cancer therapy. Trends Biotechnol. 2013 31(6): 347-354].

Pachmann, K. and U. Pachmann, Method for quantitative detection of vital epithelial tumor cells in a body fluid. 2003, US2003017514.

Roy, Anupam and Kalra, Vikram, Anticoagulation In Haemodialysis. JIMSA 2012 Vol. 25 No. 2].

Simard, L., et al., Means for the biological purification of a biological fluid. 2001, U.S. Pat. No. 6,260,715 B1

Yoshioka, S., Cell treatment device, cell treatment cartridge and body fluid treatment system. 2010, U.S. Pat. No. 9,526,823 B2.

The invention claimed is:

1. An extracorporeal blood treatment method for removal of pathogenic cells from blood of a mammalian patient, said method comprising:
   pumping blood from the patient into a blood treatment device comprising a plurality of hollow fibers, each hollow fiber having a predetermined length and a wall in the form of a semi-permeable membrane with a pore size of at most 1 micron or a pore cut off value of at most 50 kDa, wherein said membrane is made of a biocompatible material;
   providing a counter-current dialysate fluid flow in contact with an outer surface of the semi-permeable membrane of the hollow fibers, wherein a hydrostatic pressure inside the hollow fiber (in the blood) is higher than outside the hollow fiber (in the dialysate fluid), so that convective flow is provided from inside of the hollow fibers to a space outside the hollow fibers due to the hydrostatic pressure difference between the blood and the dialysate and due the pore size, whereby the pathogenic cells are moved towards the membrane;
   wherein an inner diameter of the hollow fibers are in the range of 100 to 400 microns,
   wherein at least a part of inner surfaces of the semi-permeable membrane contacting the blood is coated with a binding agent specific for binding the pathogenic cells flowing/present in a blood stream; and
   wherein a linear flow velocity of $1.8 \times 10^{-5}$ m/s to $7 \times 10^{-5}$ m/s of the blood is maintained along a longitudinal axis of the fibers and
whereby said pathogenic cells are bound by the binding agent and clusters of pathogenic cells are formed on the membrane surface of the hollow fibers once a pathogenic cell is bound by the binding agent, thereby cleansing the blood, and
leading cleansed blood back to the patient.

2. The method according to claim 1 wherein the pathogenic cells are circulating cancer cells, and wherein the circulating cancer cells bind further circulating cancer cells.

3. The method according to claim 2 wherein the membrane also comprises capture cells attached to the binding agents, said capture cells having an affinity to the circulating pathogenic cells whereby the pathogenic cells are captured by the capture cells; wherein
   the pathogenic cells are circulating tumor cells (CTCs),
   the capture cells are capture tumor cells which are capable of forming clusters (multi-cell affinity conjugates) with the circulating tumor cells wherein the capture tumor cells are derived from a tumor from said patient.

4. The method according to claim 2 wherein said clusters consist of at least 2 cells.

5. The method according to claim 4 wherein the cluster comprises 3 to 20 cells.

6. The method according to claim 2 wherein the binding agent is selected from a group of binding agents consisting of
   proteins with specific binding site(s); glycoproteins; oligonucleotide binding agents, small binding ligands and any combinations of thereof,
   proteins having a binding site specific for the pathogenic cell and wherein non-specific binding sites are covered by an inert protein,
   antibodies or a binding fragment thereof or a biomolecule having a binding region of an antibody.

7. The method according to claim 6 wherein
   the proteins with specific binding site(s) are antibodies;
   the glycoproteins are mucins and/or lectins;
   the oligonucleotide binding agents are aptamers;
   the binding ligand is folic acid; and/or
   the inert protein is albumin.

8. The method according to claim 6 wherein
   the binding region is the binding region of a tumor specific antibody.

9. The method according to claim 1 wherein the mammalian patient is selected from the group consisting of
   a patient with cancer,
   a patient after operation for removing tumor,
   a patient in need of prevention of tumor metastasis,
   a patient under chemotherapy or radiation therapy, and
   a patient during surgery i.e. during the removal of the tumor and surrounding tissue.

10. The method according to claim 9 wherein the mammalian patient is a human patient and the binding agent is a tumor specific antibody.

11. The method according to claim 10 wherein
   the method is a hemodialysis method,
   wherein the blood comprises an anticoagulation agent,
   and wherein said semi-permeable membrane is a hemodialysis membrane, wherein the pore size of the membrane of the hollow fibers ranges between 0.001 micron and 1 micron.

12. The method according to claim 1 wherein the membrane is a semi-permeable membrane for removal of circulating tumor cells (CTCs) from blood of a mammalian patient; said membrane
- having a pore size of at most 1 micron or a pore cut off value of at most 50 kDa;
- the surface of the semi-permeable membrane contacting the blood is coated with a binding agent specific for binding of the CTCs present in the blood stream.

13. The method according to claim 1 wherein the mammalian patient is a human patient.

14. The method according to claim 1 wherein the pathogenic cells are circulating tumor cells (CTC).

15. The method according to claim 1 wherein the pore cut off value is at most 30 kDa.

* * * * *